United States Patent
Murphy et al.

(10) Patent No.: US 7,327,862 B2
(45) Date of Patent: Feb. 5, 2008

(54) SYSTEM AND METHOD FOR FACILITATING CARDIAC INTERVENTION

(75) Inventors: Gregory Murphy, Richardson, TX (US); Albert Davis, Richardson, TX (US); Mitta Suresh, Richardson, TX (US)

(73) Assignee: Chase Medical, L.P., Richardson, TX (US)

( * ) Notice: Subject to any disclaimer, the term of this patent is extended or adjusted under 35 U.S.C. 154(b) by 997 days.

(21) Appl. No.: 10/135,465

(22) Filed: Apr. 30, 2002

(65) Prior Publication Data

US 2005/0020929 A1   Jan. 27, 2005

Related U.S. Application Data

(60) Provisional application No. 60/288,173, filed on Apr. 30, 2001, provisional application No. 60/307,218, filed on Jul. 20, 2001, provisional application No. 60/318,024, filed on Sep. 7, 2001, provisional application No. 60/357,559, filed on Feb. 15, 2002, provisional application No. 60/307,215, filed on Jul. 20, 2001.

(51) Int. Cl.
*G06K 9/00* (2006.01)

(52) U.S. Cl. .............................. 382/128; 128/922; 378/4
(58) Field of Classification Search ................ 382/100, 382/128–133; 128/922; 378/4
See application file for complete search history.

(56) References Cited

U.S. PATENT DOCUMENTS

| | | | |
|---|---|---|---|
| 4,436,684 A | 3/1984 | White | |
| 5,072,384 A | 12/1991 | Doi et al. | |
| 5,151,856 A * | 9/1992 | Halmann et al. | 600/508 |
| 5,235,510 A | 8/1993 | Yamada et al. | |
| 5,239,591 A | 8/1993 | Ranganath | |
| 5,273,038 A | 12/1993 | Beavin | |
| 5,319,551 A | 6/1994 | Sekiguchi et al. | |
| 5,360,006 A | 11/1994 | Geiser et al. | |
| 5,375,156 A | 12/1994 | Kuo Petravic et al. | |
| 5,433,199 A | 7/1995 | Cline et al. | |
| 5,435,310 A * | 7/1995 | Sheehan et al. | 600/416 |

(Continued)

FOREIGN PATENT DOCUMENTS

WO           116886           3/2001

OTHER PUBLICATIONS

F.P. van Rugge et al., "Magnetic Resonance Imaging during dobutamine Stress for detection and localization of coronary artery disease" *Circulation* 1994; 90, No. 1, pp. 127-138.

(Continued)

*Primary Examiner*—Bhavesh M Mehta
*Assistant Examiner*—Anand Bhatnagar
(74) *Attorney, Agent, or Firm*—Meyertons, Hood, Kivlin, Kowert & Goetzel, P.C.

(57) ABSTRACT

One embodiment discloses a computerized method of facilitating cardiac intervention, comprising inputting patient data, creating a computerized interactive model of a diseased heart based on the patient data, wherein the model comprises structural elements, simulating at least one proposed cardiac intervention treatment by adding or deleting structural elements to the model, and determining the effects of the proposed cardiac simulation upon the entire model. Simulations may be repeated to allow the user to determine an optimal cardiac intervention. Additionally, a template may be created from the model to use as a guide during the cardiac intervention.

44 Claims, 39 Drawing Sheets

U.S. PATENT DOCUMENTS

| | | | |
|---|---|---|---|
| 5,450,850 A | 9/1995 | Iinuma | |
| 5,509,084 A | 4/1996 | Tanaka | |
| 5,533,085 A | 7/1996 | Sheehan et al. | |
| 5,559,901 A | 9/1996 | Lobregt | |
| 5,570,430 A | 10/1996 | Sheehan et al. | |
| 5,601,084 A | 2/1997 | Sheehan et al. | |
| 5,633,951 A | 5/1997 | Moshfeghi | |
| 5,684,398 A | 11/1997 | Takiguchi et al. | |
| 5,687,737 A | 11/1997 | Branham et al. | |
| 5,704,791 A | 1/1998 | Gillio | |
| 5,734,739 A | 3/1998 | Sheehan et al. | |
| 5,755,577 A | 5/1998 | Gillio | |
| 5,757,877 A | 5/1998 | Wilting | |
| 5,779,634 A | 7/1998 | Ema et al. | |
| 5,791,908 A | 8/1998 | Gillio | |
| 5,800,177 A | 9/1998 | Gillio | |
| 5,800,178 A | 9/1998 | Gillio | |
| 5,807,256 A | 9/1998 | Taguchi et al. | |
| 5,817,022 A | 10/1998 | Vesely | |
| 5,839,440 A | 11/1998 | Liou et al. | |
| 5,889,524 A | 3/1999 | Sheehan et al. | |
| 5,892,515 A | 4/1999 | Kobayashi et al. | |
| 5,902,239 A | 5/1999 | Buurman | |
| 5,920,660 A | 7/1999 | Goto | |
| 5,923,770 A | 7/1999 | O'Donnell et al. | |
| 5,947,899 A | 9/1999 | Winslow et al. | |
| 5,954,648 A | 9/1999 | Van Der Brug | |
| 5,963,211 A | 10/1999 | Oikawa et al. | |
| 6,024,705 A | 2/2000 | Schlager et al. | |
| 6,045,512 A | 4/2000 | Roteliuk et al. | |
| 6,047,090 A | 4/2000 | Makram-Ebeid | |
| 6,106,466 A | 8/2000 | Sheehan et al. | |
| 6,185,447 B1 | 2/2001 | Alley et al. | |
| 6,190,320 B1 | 2/2001 | Lelong | |
| 6,201,165 B1 * | 3/2001 | Grant et al. | 800/3 |
| 6,205,349 B1 | 3/2001 | Kim et al. | |
| 6,205,411 B1 | 3/2001 | DiGioia, III et al. | |
| 6,230,048 B1 | 5/2001 | Selvester et al. | |
| 6,241,699 B1 | 6/2001 | Suresh et al. | |
| 6,268,730 B1 | 7/2001 | Du | |
| 6,298,112 B1 | 10/2001 | Acharya et al. | |
| 6,315,735 B1 | 11/2001 | Joeken et al. | |
| 6,346,940 B1 | 2/2002 | Fukunaga | |
| 6,366,684 B1 | 4/2002 | Gerard et al. | |
| 6,373,920 B1 | 4/2002 | Hsieh | |
| 6,415,048 B1 | 7/2002 | Schneider | |
| 6,421,565 B1 | 7/2002 | Hemmingsson | |
| 6,438,403 B1 * | 8/2002 | Cline et al. | 600/410 |
| 6,442,417 B1 | 8/2002 | Shahidi et al. | |
| 6,445,183 B1 | 9/2002 | Shimizu et al. | |
| 6,447,453 B1 | 9/2002 | Chenal et al. | |
| 6,447,454 B1 | 9/2002 | Chenal et al. | |
| 6,454,712 B1 | 9/2002 | Oonuki | |
| 6,454,776 B1 | 9/2002 | Tajima et al. | |
| 6,468,218 B1 | 10/2002 | Chen et al. | |
| 6,470,070 B2 | 10/2002 | Menhardt | |
| 6,473,488 B2 | 10/2002 | Menhardt | |
| 6,473,634 B1 | 10/2002 | Barni | |
| 6,482,146 B1 | 11/2002 | Alferness et al. | |
| 6,487,432 B2 | 11/2002 | Slack | |
| 6,493,571 B1 | 12/2002 | Bis et al. | |
| 6,496,560 B1 | 12/2002 | Lin et al. | |
| 6,510,337 B1 | 1/2003 | Heuscher et al. | |
| 6,522,324 B1 | 2/2003 | Bosma et al. | |
| 6,526,307 B2 | 2/2003 | Foo | |
| 6,535,623 B1 * | 3/2003 | Tannenbaum et al. | 382/128 |
| 6,545,678 B1 * | 4/2003 | Ohazama | 345/427 |
| 6,557,558 B1 | 5/2003 | Tajima et al. | |
| 6,559,641 B2 | 5/2003 | Thesen | |
| 6,563,941 B1 | 5/2003 | O Donnell et al. | |
| 6,573,717 B2 | 6/2003 | Thesen | |
| 6,574,304 B1 | 6/2003 | Hsieh et al. | |
| 6,587,541 B2 | 7/2003 | Menhardt | |
| 6,608,916 B1 | 8/2003 | Wei et al. | |
| 6,608,917 B1 | 8/2003 | Wei et al. | |
| 6,628,743 B1 | 9/2003 | Drummond et al. | |
| 2001/0012913 A1 | 8/2001 | Iliff | |
| 2001/0029333 A1 | 10/2001 | Shahidi | |
| 2001/0031919 A1 | 10/2001 | Strommer et al. | |
| 2001/0036245 A1 | 11/2001 | Kienzle, III et al. | |
| 2002/0016541 A1 | 2/2002 | Glossop | |
| 2002/0031204 A1 | 3/2002 | Vilsmeier | |
| 2002/0032377 A1 | 3/2002 | Thesen | |
| 2002/0035321 A1 | 3/2002 | Bucholz et al. | |
| 2002/0042566 A1 | 4/2002 | Matsuzaki et al. | |
| 2002/0070970 A1 | 6/2002 | Wood et al. | |
| 2002/0077540 A1 | 6/2002 | Kienzle, III | |
| 2002/0077541 A1 | 6/2002 | Kienzle, III | |
| 2002/0082498 A1 | 6/2002 | Wendt et al. | |
| 2002/0087075 A1 | 7/2002 | Bucholz | |
| 2002/0095313 A1 | 7/2002 | Haq | |
| 2002/0127523 A1 | 9/2002 | Edic et al. | |
| 2002/0167533 A1 | 11/2002 | Tirumalai et al. | |
| 2003/0000535 A1 | 1/2003 | Galloway, Jr. et al. | |
| 2003/0018251 A1 | 1/2003 | Solomon | |
| 2003/0038802 A1 | 2/2003 | Johnson et al. | |
| 2003/0069494 A1 | 4/2003 | Jolly | |
| 2003/0078494 A1 | 4/2003 | Panescu et al. | |
| 2003/0095697 A1 | 5/2003 | Wood et al. | |
| 2003/0114750 A1 | 6/2003 | Brock Fisher et al. | |
| 2003/0187362 A1 | 10/2003 | Murphy et al. | |
| 2004/0049115 A1 | 3/2004 | Murphy et al. | |
| 2004/0049116 A1 | 3/2004 | Murphy et al. | |
| 2004/0153128 A1 | 8/2004 | Murphy et al. | |
| 2004/0176678 A1 | 9/2004 | Murphy et al. | |
| 2004/0176679 A1 | 9/2004 | Murphy et al. | |
| 2005/0043609 A1 | 2/2005 | Murphy et al. | |

OTHER PUBLICATIONS

Antman, Elliott M. et al., "Abciximab Facilitates the Rate and Extent of Thrombolysis-Results of the Thrombolysis in Myocardial Infarction (TIMI) 14 Trial", *Circulation*, Jun. 1, 1999, pp. 2720-2732.

Keegan, Jennifer et al., "Interleaved Spiral Cine Coronary Artery Velocity Mapping", *Magnetic Resonance in Medicine*, vol. 43, 2000, pp. 787-792.

Medina, R. et al., "Reconstruction of Three-Dimensional Shapes in Biplane Angiography: a Fuzzy and Evolutionary Approach", *Computers in Cardiology*, Hannover, Germany, Sep. 26, 1999, pp. 663-666.

Miles, K.A., "Measurement of tissue perfusion by dynamic computed tomography", *The British Journal of Radiology*, 1991, vol. 64, No. 761, pp. 409-412.

Mochizuki, Teruhito et al., "Demonstration of Acute Myocardial Infarction by Subsecond Spiral Computed Tomography-Early Defect and Delayed Enhancement", *Circulation*, 1999, 99, pp. 2058-2059.

Rumberger, John A. et al., "Use of Ultrafast Computed Tomography to Quantitate Regional Myocardial Perfusion: A Preliminary Report", *Journal of the American College of Cardiology*, vol. 9, No. 1, Jan. 1987, pp. 59-69.

J.M. Guccione et al., "Passive Material Properties of Intact Ventricular Myocardium Determined from a Cylindrical Model" *Journal of Biomechanical Engineering*, vol. 113, Feb. 1991.

K.D. Costa et al., "A Three-Dimensional Finite Element Method for Large Elastic Deformations of Ventricular Myocardium: I-Cylindrical and Spherical Polar Coordinates" *Journal of Biomechanical Engineering*, Nov. 1996, vol. 118, pp. 452-463.

P.J. Hunter et al., "Modeling the mechanical properties of cardiac muscle" *Progress in Biophysics & Molecular Biology*, 69 (1998) pp. 289-331.

R. Mazhari et al., "Integrative Models for Understanding the Structural Basis of Regional Mechanical Dysfunction in Ischemic Myocardium" *Annals of Biomedical Engineering*, 2000, vol. 28, pp. 979-990.

Hurst et al., "Hurst's The Heart, Arteries and Veins, 9th Edition" McGraw-Hill, 1998, Chapters 18-20, pp. 623-684.

Y. Sun et al., "A comprehensive model for right-left heart interaction under the influence of pericardium and baroreflex" *The American Journal of Physiology*, 1997, pp. H1499-H1515.

Makhijani, V. B. et al., "Three-dimensional coupled fluid—Structure simulation of pericardial bioprosthetic aortic valve function" *ASAIO Journal*, 1997, 43:M387-M392.

Olszewski, M. E., "Segmentation of Cardiac Magnetic Resonance Images Using Multidimensional Active Appearance Models", Department of Electrical and Computer Engineering, The University of Iowa, Apr. 2001.

Di Donato, M. et al. "Regional Myocardial performance of non-ischaemic zones remote from anterior wall left ventricular aneurysm—Effects of aneurysmectomy", European Heart Journal, (1995) 16, 1285-1292.

F.H. Sheehan et al., "Advantages and applications of the centerline method for characterizing regional ventricular function" *Circulation* 1986; 74, No. 2, pp. 293-305.

T.F. Cootes and C. J. Taylor, "Statistical Models of Appearance for Computer Vision" Jul. 10, 2000 http://cvl.umiacs.umd.edu/users/nanda/Academics/Academic.html.

E. R. Holman et. al., "Detection and Quantification of Dysfunctional Myocardium by Magnetic Resonance Imaging" *Circulation* 1997; vol. 95, No. 4; pp. 924-931.

Van der Geest, Rob J. et al., "Comparison Between Manual and Semiautomated Analysis of Left Ventricular Volume Parameters from Short-Axis MR Images", Journal of Computer Assisted Tomography, vol. 21, No. 5, 1997, pp. 756-765.

Weiss, Robert M. et al., "Evaluation of Cardiovascular Structure and Function with Electron-Beam Computed Tomography", Marcus Cardiac Imaging, 1996, vol. 2, Chapt. 53: 820-828.

Dai, Xiaolong et al., "Left-Ventricle Boundary Detection from Nuclear Medicine Images", (http://www4.ncsu.edu/eos/users/w/wes/homepage/daiHTML/cmrg_JDI.fm3.html#FN1) Journal of Digital Imaging, vol. 11, No. 1, Feb. 1998.

nerac.com "RetroSearch: Active Appearance Models", Question No. 1199989.009, Sep. 15, 2003.

U.S. Appl. No. 10/800,461, filed Mar. 15, 2004, Murphy et al.

U.S. Appl. No. 10/800,433, filed Mar. 15, 2004, Murphy et al.

U.S. Appl. No. 10/768,403, filed Jan. 30, 2004, Murphy et al.

U.S. Appl. No. 10/769,745, filed Jan. 30, 2004, Suresh et al.

U.S. Patent Application entitled A System and Method for Facilitating Cardiac Intervention Jan. 30, 2004 Murphy et al.

International Search Report and Written Opinion for PCT/US04/02669 mailed Feb. 3, 2005.

Written Opinion for PCT/US04/02669 mailed Feb. 3, 2005.

International Preliminary Examination Report for PCT/US04/02604 mailed Dec. 21, 2004.

International Search Report and Written Opinion for PCT/US04/02604 mailed Oct. 6, 2004.

Kim, R. J. et al. "The Use of Contrast-Enhanced Magnetic Resonance Imaging to Identify Reversible Myocardial Dysfunction" The New England Journal of Medicine, vol. 343, No. 20, Nov. 16, 2000, 1445-1452.

McEachen II, J. C. et al. "Shape-Based Tracking of Left Ventricular Wall Motion" IEEE Transactions on Medical Imaging, vol. 16, No. 3, Jun. 1997, 270-283.

Chalana, V. et al. "A Multiple Active Contour Model for Cardiac Boundary Detection on Echocardiographic Sequences" IEEE Transactions on Medical Imaging, vol. 15, No. 3 Jun. 1996, 290-298.

Setarehdan, S. K. et al. "Automatic Left Ventricular Feature Extraction and Visualisation from Echocardiographic Images" Computers in Cardiology 1996, 9-12.

Jacob G. et al. "Robust Contour Tracking in Echocardiographic Sequences" 6th International Conference on Computer Vision. ICCV '98 Bombay, Jan. 4-7, 1998 IEEE International Conference on Computer Vision, New York, NY: IEEE, US, Jan. 4, 1998, pp. 408-413.

Supplemental Search Report for PCT/US04/02604 mailed Sep. 6, 2006.

Office Action for U.S. Appl. No. 10/354,884 mailed on Nov. 1, 2006.

\* cited by examiner

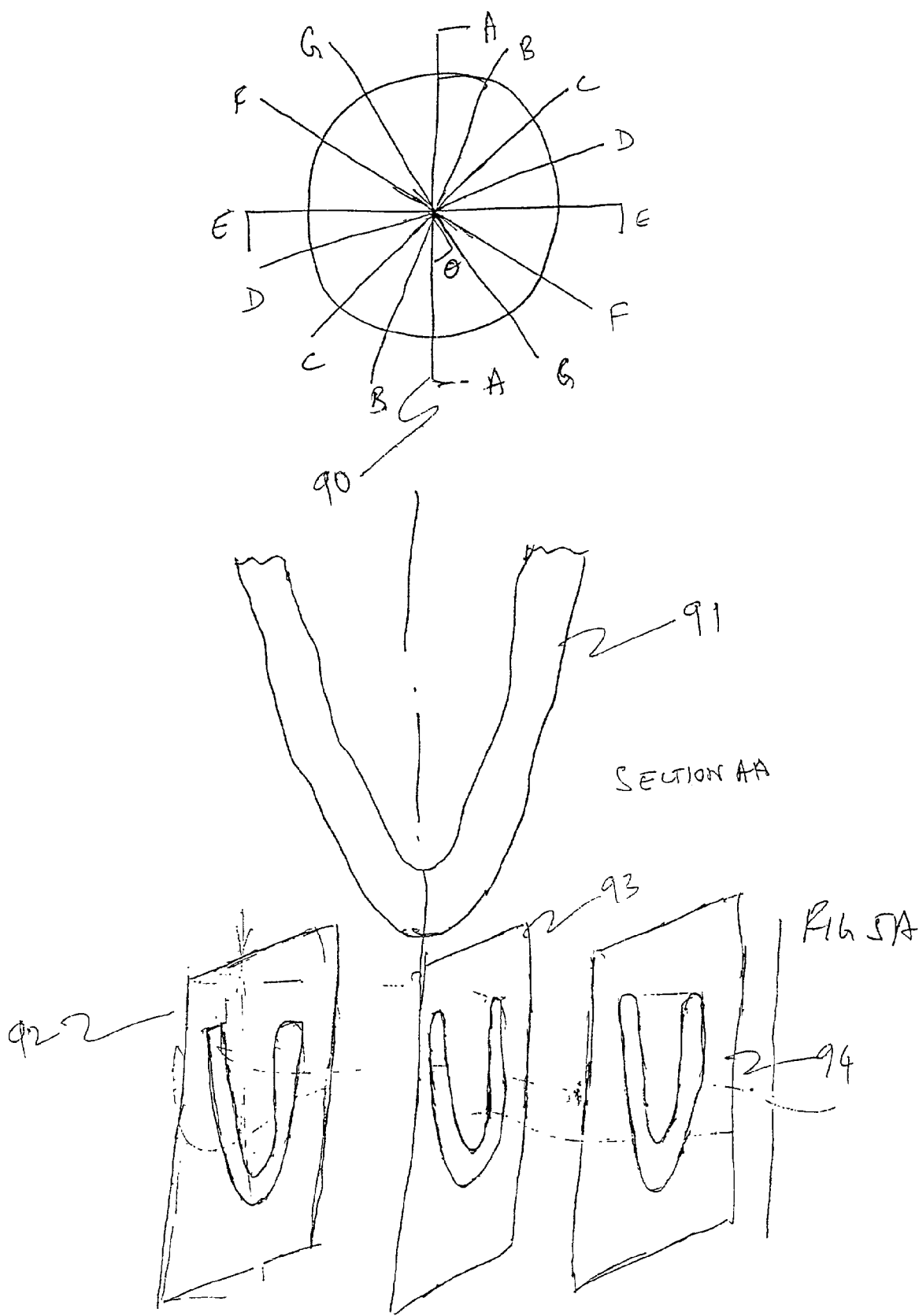

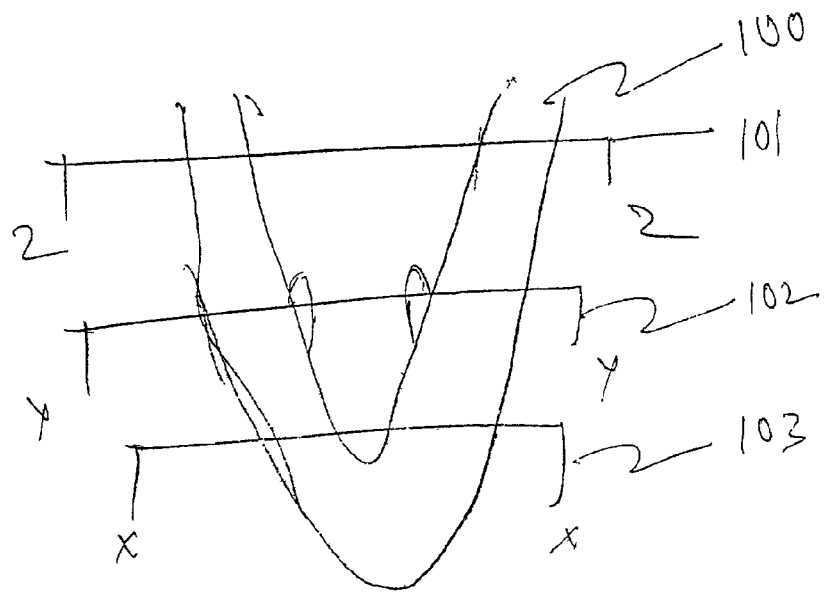
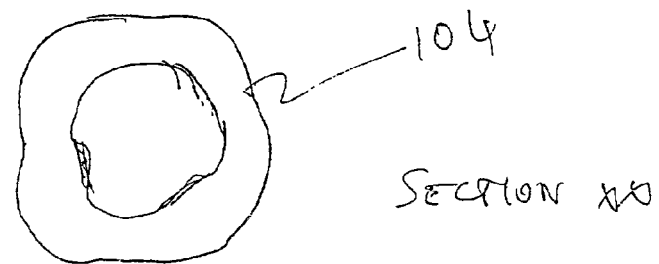
SECTION XX
FIG 5B
SECTION YY
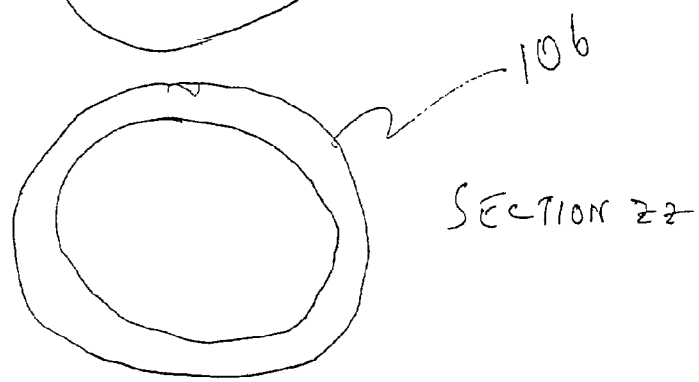
SECTION ZZ

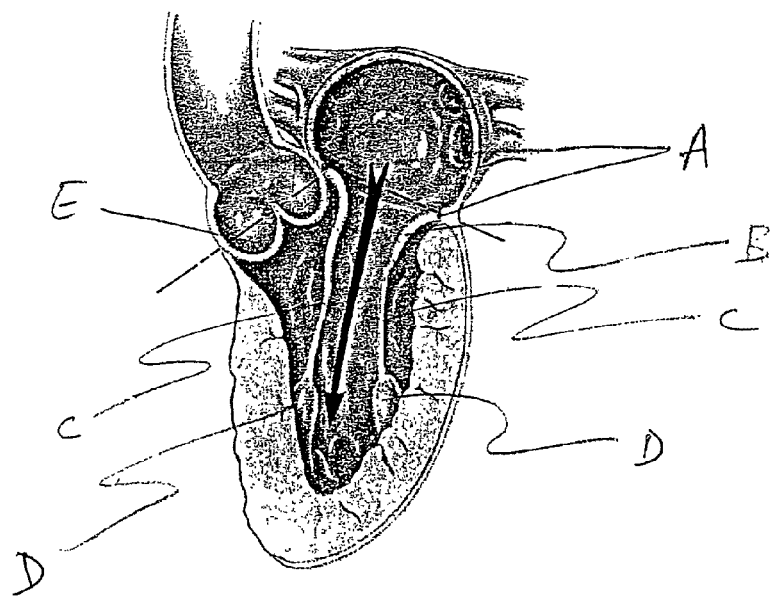
FIGURE 11
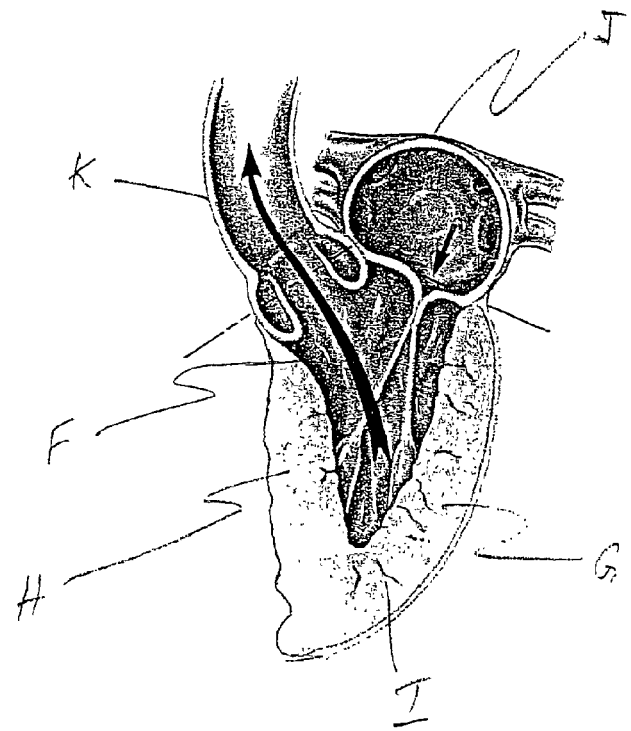

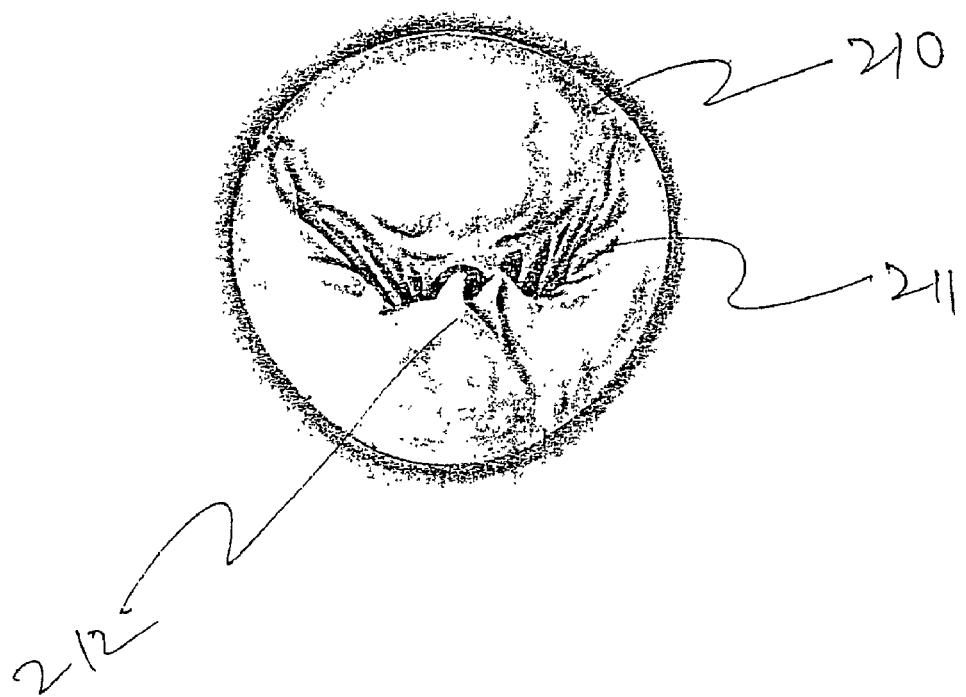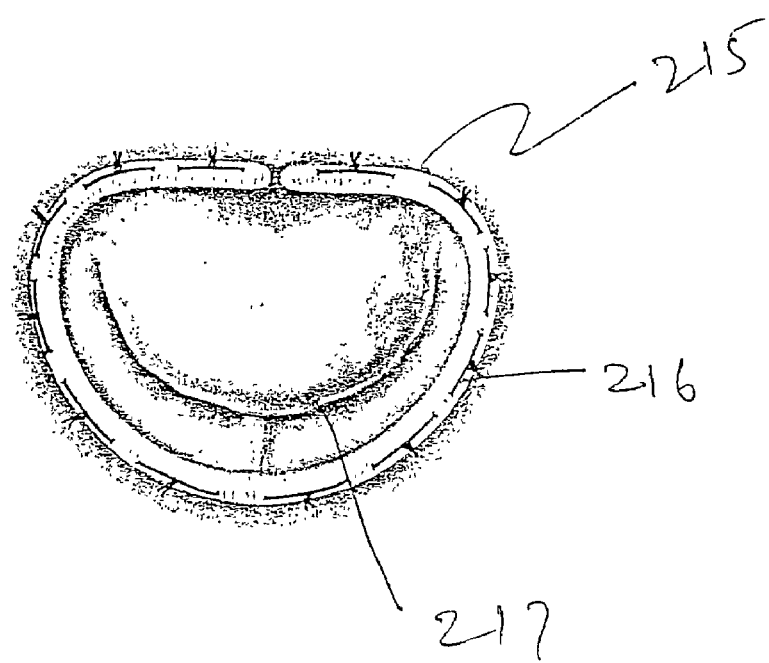
FIGURE 13D

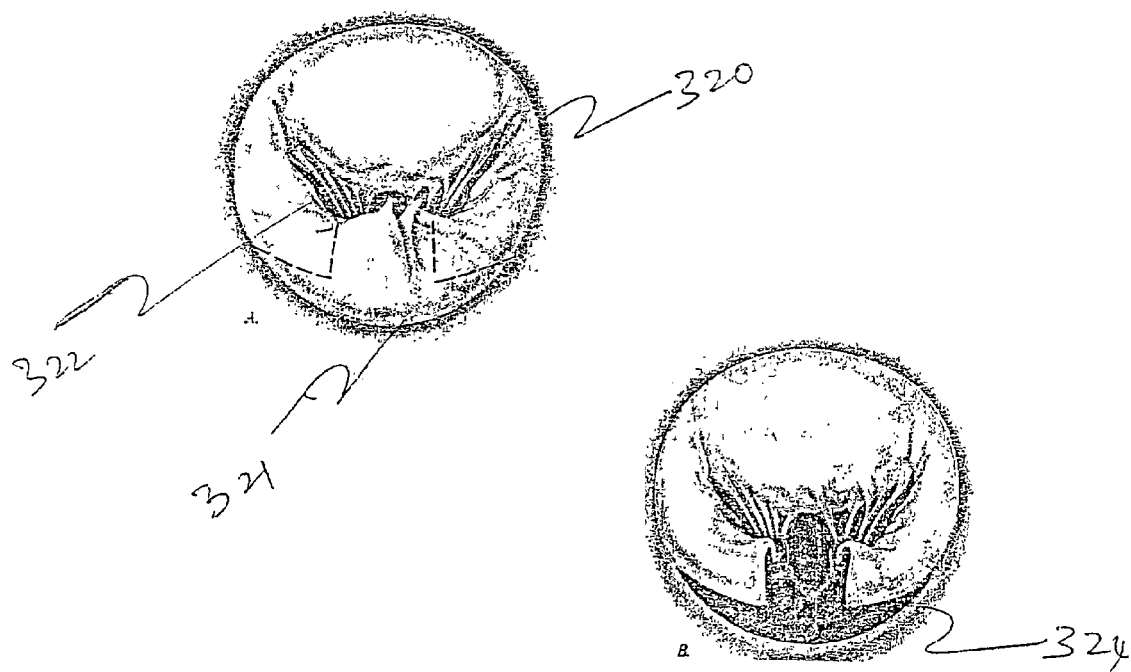
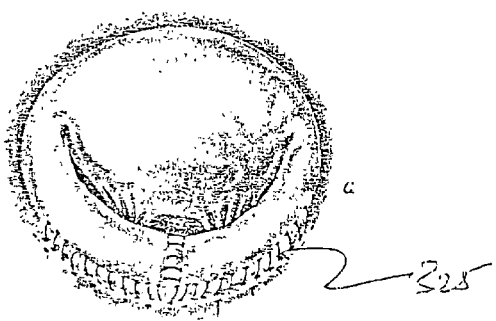
FIGURE 130

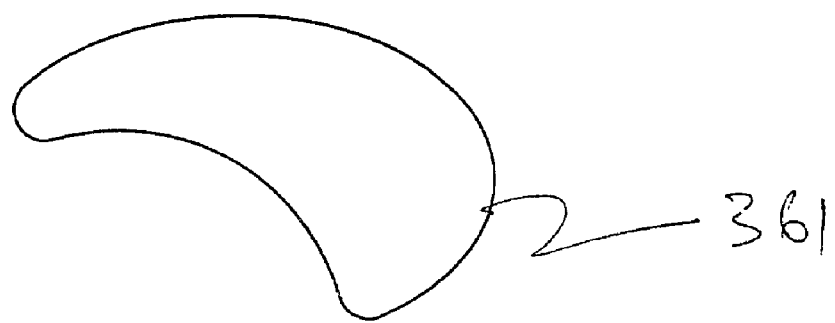
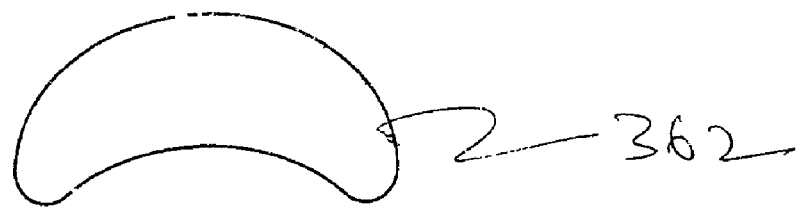
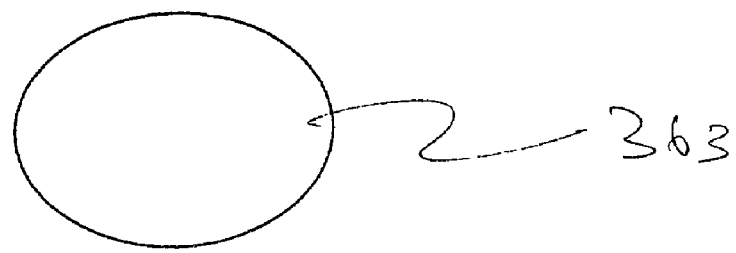
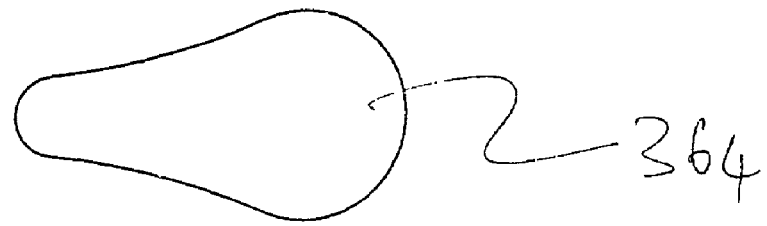
FIGURE 19

$\varepsilon_x \neq \varepsilon_y$ $\varepsilon$ = MODULUS OF ELASTICITY

SYSTEM AND METHOD FOR FACILITATING CARDIAC INTERVENTION

CROSS-REFERENCE

This application claims priority to U.S. Provisional Patent Application Ser. No. 60/288,173 filed on Apr. 30, 2001, U.S. Provisional Patent Application Ser. No. 60/307,218 filed on Jul. 20, 2001, U.S. Provisional Patent Application Ser. No. 60/318,024 filed on Sep. 7, 2001, and U.S. Provisional Patent Application Ser. No. 60/357,559 filed on Feb. 15, 2002, the disclosures of which are hereby incorporated by reference, and claims the benefit of U.S. Provisional Patent Application Ser. No. 60/307,215 filed on Jul. 20, 2001.

TECHNICAL FIELD

This invention relates generally to systems for identifying the structural elements that contribute to the cardiac performance of an individual patient through the use of imaging methods, and in particular to a computerized system and method for facilitating cardiac intervention methods.

BACKGROUND

The circulatory system of a human works as a closed system where the effects of one part of the system are felt by all other parts of the system. For example, if a person's blood pressure rises then there is a corresponding pressure decrease in the venous system, the decrease is much smaller than the increase in the arterial side because of the fact that venous vasculature is more compliant than the arterial vasculature. Within the circulatory system the key component is the heart. Any change to any component of the heart will have an effect felt throughout the entire system.

The function of a heart in an animal is primarily to deliver life-supporting oxygenated blood to tissue throughout the body. This function is accomplished in four stages, each relating to a particular chamber of the heart. Initially deoxygenated blood is received in the right auricle of the heart. This deoxygenated blood is pumped by the right ventricle of the heart to the lungs where the blood is oxygenated. The oxygenated blood is initially received in the left auricle of the heart and ultimately pumped by the left ventricle of the heart throughout the body. It may be seen that the left ventricular chamber of the heart is of particular importance in this process as it pumps the oxygenated blood through the aortic valve and ultimately throughout the entire vascular system.

A myocardial infarction (heart attack) will not affect two people in the same manner. The extent of the damage due to the infarction will be based on many factors, such as; location of the infarction, extent of collateral flow in the blockage area, health of the heart prior to infarction, etc. The unique damage will have a corresponding unique effect on the entire cardiac system. The infarction damage in one patient may be isolated to a small section of the ventricle wall. In another person the infarction may involve not only the ventricle wall but also the septum. In still another person the infarction might involve the papillary muscles. Over time these unique damages will cause the heart to respond in different ways to compensate for the damage in an attempt to keep the system operating as best it can.

Various treatments are currently employed to repair, replace or mitigate the effects of damaged components of the heart. Some of these treatments involve grafting new arteries onto blocked arteries, repairing or replacing valves, reconstructing a dilated left ventricle, administering medication treatment or implanting mechanical devices. All these treatments apply standard repairs to unique problems with a minimum of analysis as to what the optimum intervention should involve. None of the current procedures involve analyzing the performance of the cardiac system after the treatment to see what effect the treatment has had on the entire system. For example, a patient with blocked arteries may undergo the placement of 5-6 grafts on his heart due solely to a short visual inspection of angiographic films that show some stenosis of the arteries of the heart. No analysis is performed to see if placing 3-4 grafts will achieve the same perfusion of the myocardium as the 5-6 grafts. It is simply a situation where the doctor decides that more is better, which may not be true. Placing 5-6 grafts requires more surgical time, longer pump runs and incisions into numerous areas of the body to recover the needed grafts. This increases morbidity to the patient and may contribute to death of the patient who may not tolerate the additional stress of a longer, more invasive procedure. On some patients the extra grafts may be needed, since collateral flow or flow from other arteries is not sufficient to perfuse the entire myocardium, while on other patients the grafts are not needed, since sufficient flows will be generated from fewer grafts. Currently, the doctor has no way of knowing if the total number of grafts that he put in was necessary.

A similar procedure is used to place stents in a vessel. Stents are placed in vessels based on an assessment of blockage and ability to access the obstructed area. No method of analysis is performed to determine the effects of placing a stent, or to analyze how many stents should be placed where, or to determine if stenting produces a better result than bypassing.

The current process for repairing and replacing valves also heavily rely on the doctor's knowledge and intuition. There is no precise way to determine how much a valve or structural component needs to change or what the effect of that change will be, The current procedure for determining if the correct repair was made is to complete the repair, remove the patient from cardiopulmonary bypass and let the heart start beating. When the heart's performance reaches a normal range, an echocardiography is taken of the valve to ensure that it is not regurgitant. If the repair left some regurgitation, then the patient must go back on cardiopulmonary bypass, the heart must be stopped again, reopened and a repair made to the repair or replacement. The checking procedure is repeated after the second repair to ensure that the procedure has been correctly done. This procedure subjects the patient to unnecessary risks by exposing them to longer than necessary bypass runs and reperfusion injuries each time the heart is weaned of cardioplegia, and takes up valuable operating room and staff time. The repairs to repairs scenario for valve procedures is not uncommon. Additionally this assessment method only assesses one factor related to the performance of the valve and ventricle, regurgitation. A doctor may perform a procedure, which corrects the existing problem, but creates another problem or diminishes the performance of the ventricle. The doctor has little if any way of know if he compromised ventricle performance, since current analytical tools only look for flow across the valve. Methods to identify and evaluate the positioning of the valve apparatus and the attached tissue and their combined performance are nonexistent.

Similarly, there is no method to determine when to replace or repair a valve. This is left to the judgment of the doctor based on review of two dimensional echocardiography studies. Doctors who are unfamiliar with repair techniques may opt for replacement when repair is not only possible but also when repair is the best course of action for the patient. The replacement will be done without knowing what effect it will have on the other elements of the mitral valve apparatus, left ventricle, left atrium and the overall functioning of the heart. A replacement that attaches the chordae tendinae to the new valve may have a much different effect on the ventricle than a replacement that excludes the chordae tendinae. Currently there is no method to assist the doctor in making this assessment. Repairs are typically undertaken to shorten the chordae and annulus without knowing what effect the repairs will have on the entire apparatus. The current solution is experimentation on the patient in real time; make the repair and let the heart beat to see what the repair has done.

What is needed therefore is a reliable method and apparatus to allow a doctor to determine which elements of the heart are not contributing to, or are decrementing from, the performance of the heart, and a method and apparatus to allow the doctor to simulate the treatment on a portion of those elements and see the effect the treatment has on the other elements and the heart as a whole.

BRIEF SUMMARY

One embodiment discloses a computerized system and method of facilitating cardiac intervention, comprising inputting patient data, creating a computerized interactive model of a diseased heart based on the patient data, wherein the model comprises structural elements, simulating at least one proposed cardiac intervention treatment by adding or deleting structural elements to the model, and determining the effects of the proposed cardiac simulation upon the entire model. Simulation may be repeated to allow the user to determine an optimal cardiac intervention. Additionally, a template may be created from the model to use as a guide during the cardiac intervention.

Some embodiments are directed to the preoperative analysis of a patient's heart condition and computer assisted manipulation preoperatively of the patient's heart to perform procedures such as coronary artery bypass grafting, stent placement, surgical ventricular repair, valve repair and replacement and numerous other procedures some involving the use of implantable devices.

BRIEF DESCRIPTION OF THE DRAWINGS

The above brief description as well as further objects, features and advantages of the methods and apparatus of the present invention will be more fully appreciated by reference to the following detailed description of presently preferred but nonetheless illustrative embodiments in accordance with the present invention when taken in conjunction with the accompanying drawings in which:

FIG. 5A: Illustrates sectional views of MRI and Echocardiography (long axis).

FIG. 5B: Illustrates sectional views of MRI and Echocardiography (short axis).

FIG. 11: Illustrates an embodiment of different structural elements of a heart.

FIG. 19: Illustrates an embodiment of various potential patches of different sizes and shapes to seal an opening in a ventricle.

Figure 1:
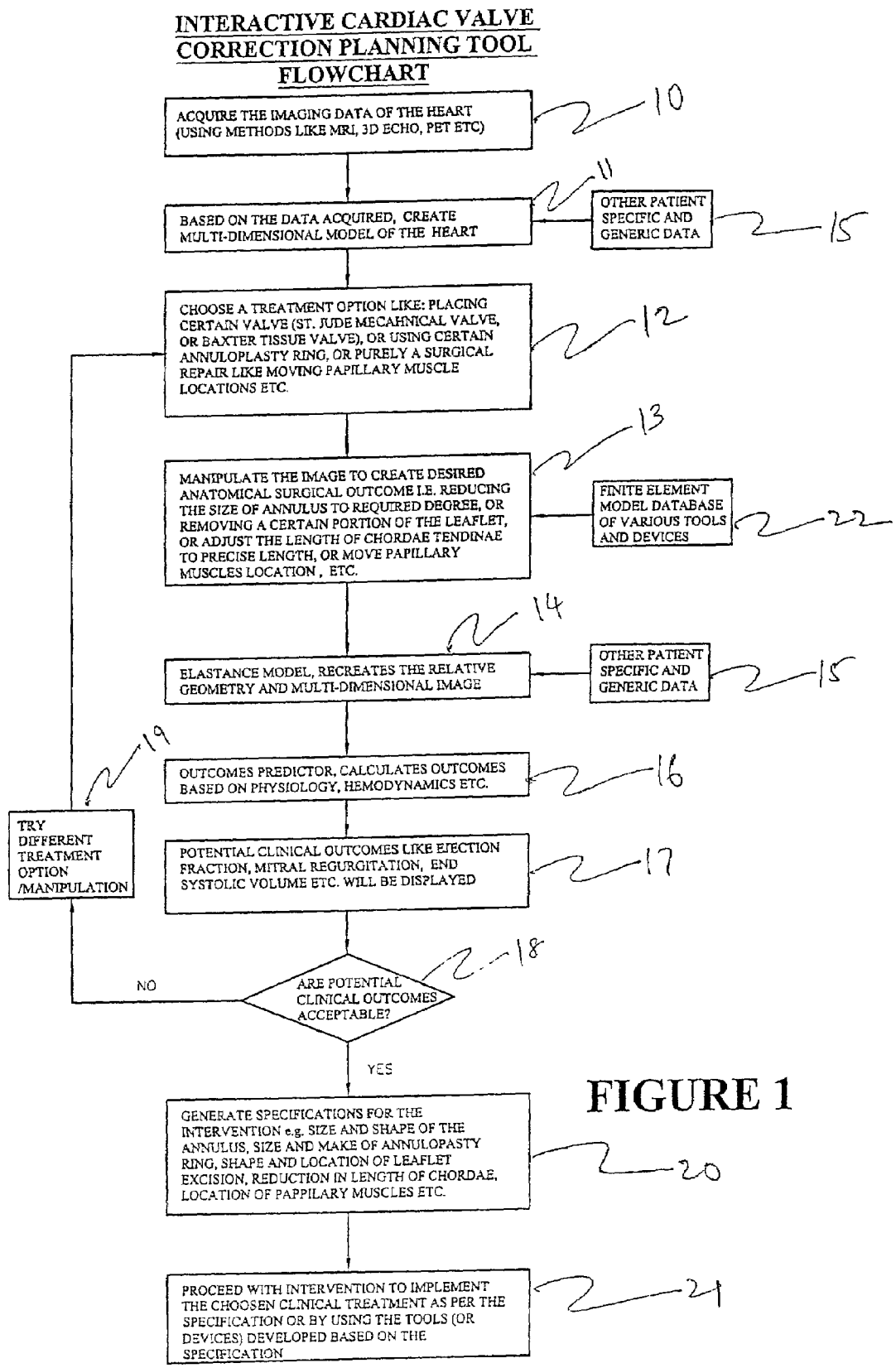
FIG. 1 is a flowchart illustrating one embodiment of a method of a cardiac intervention.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

Figure 5:
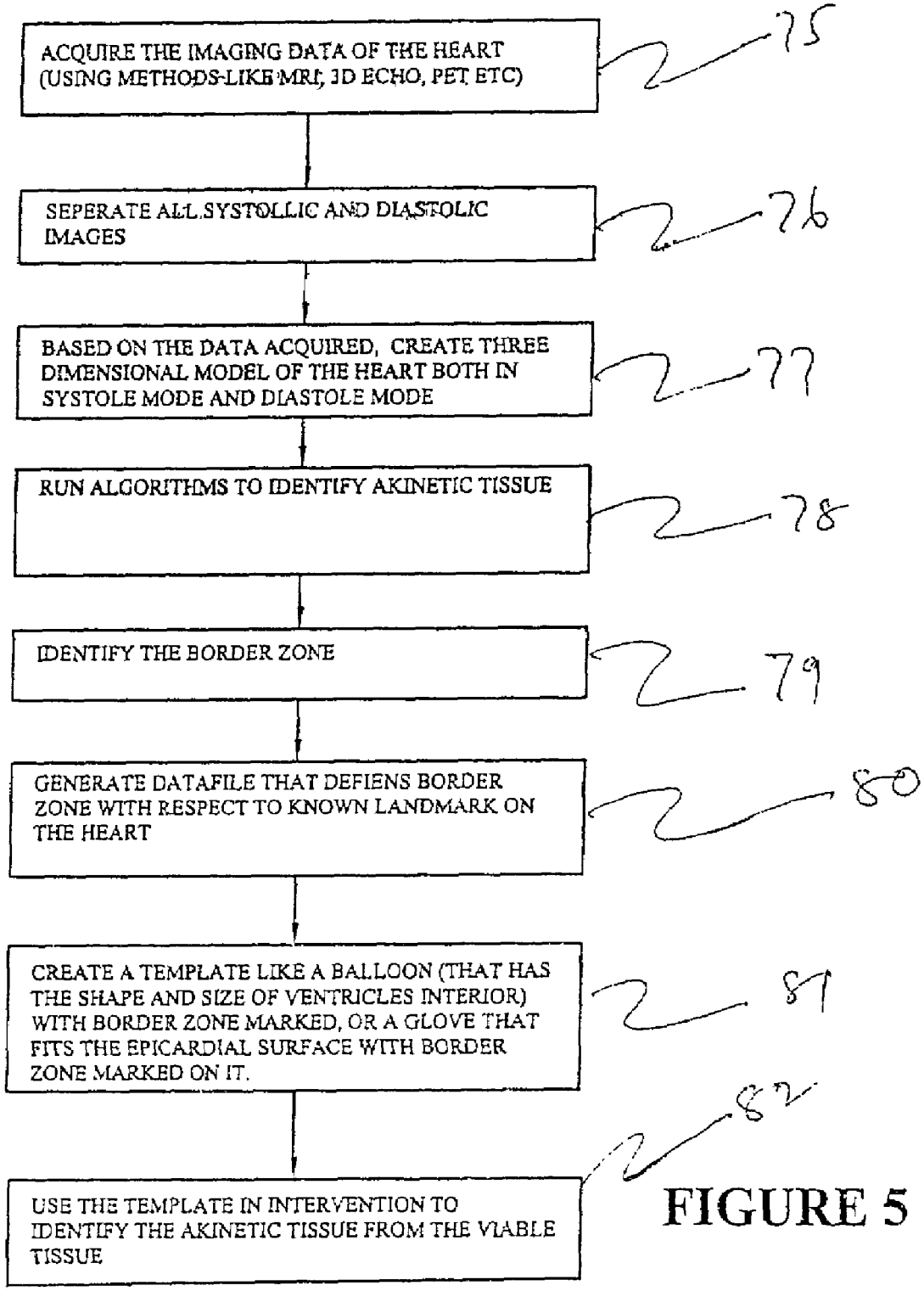
FIG. 5 is a flowchart illustrating one embodiment of a method of a cardiac intervention.
Figure 6:
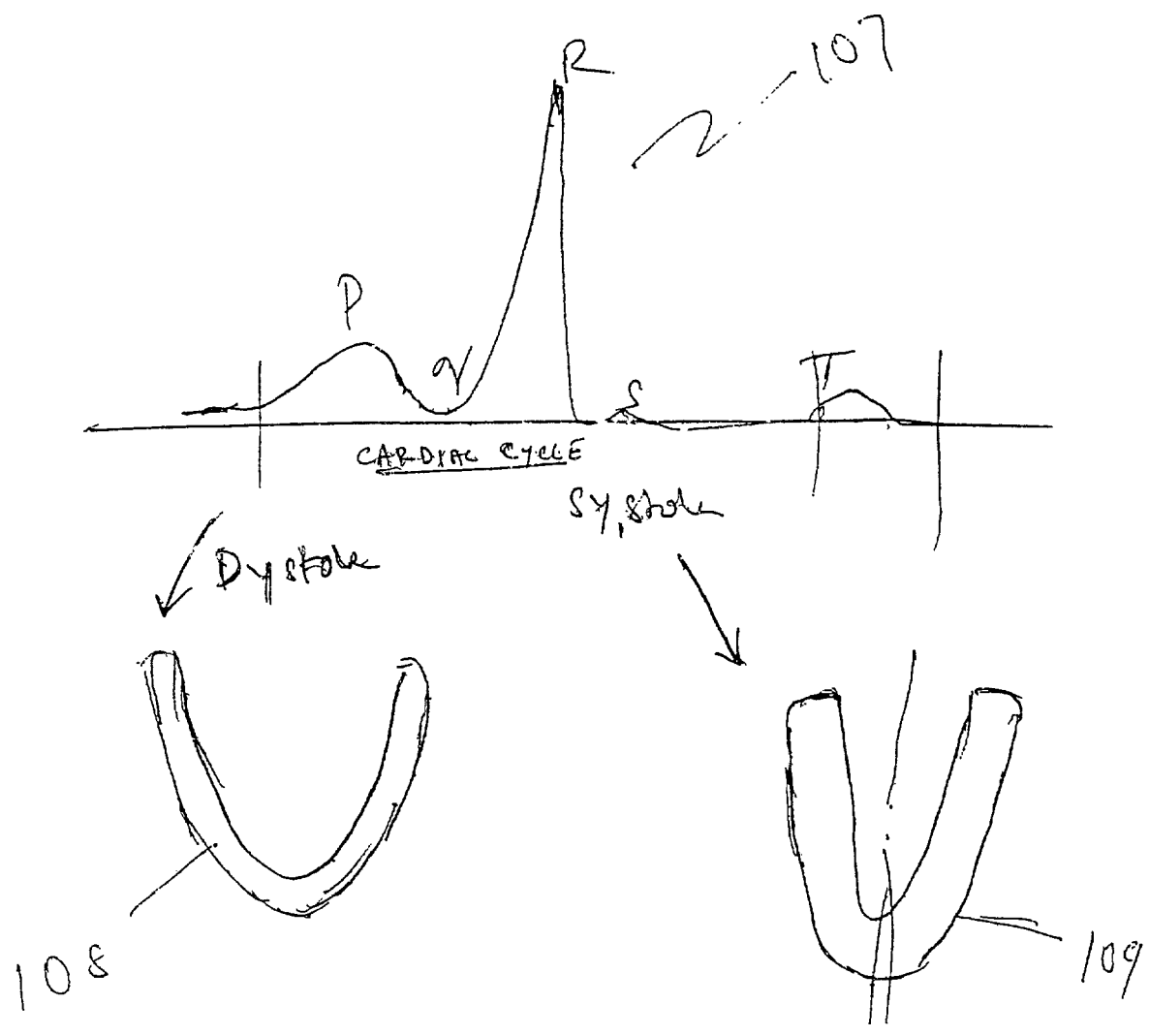
FIG. 6: Illustrates an embodiment of a heart in various stages of a cardiac cycle.
Figure 10:
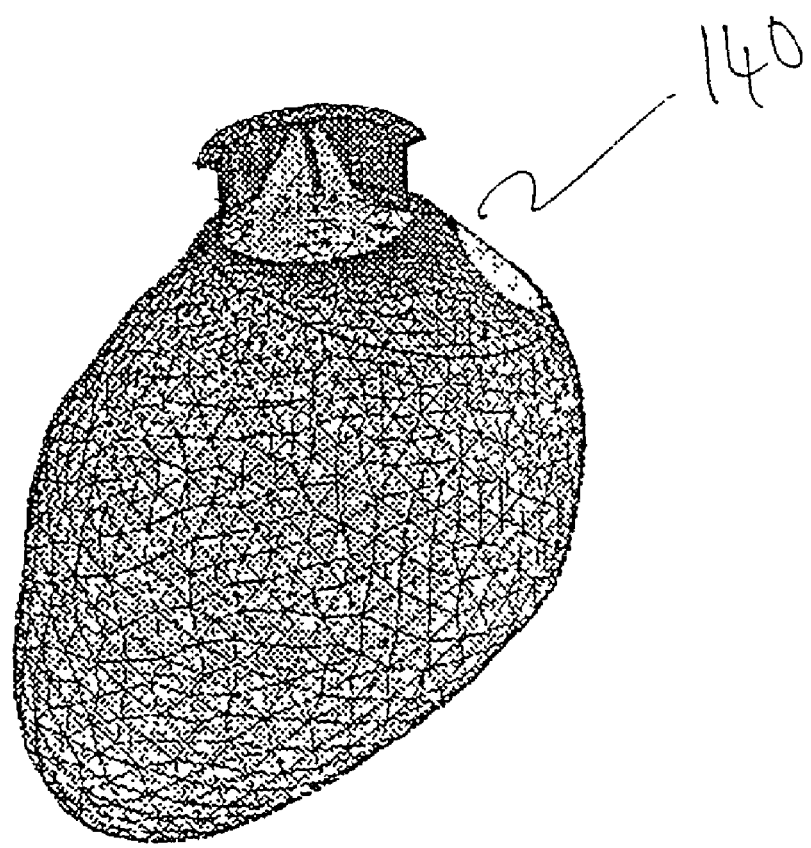
FIG. 10: Illustrates an embodiment of a model with a finite element grid.
Figure 12A:
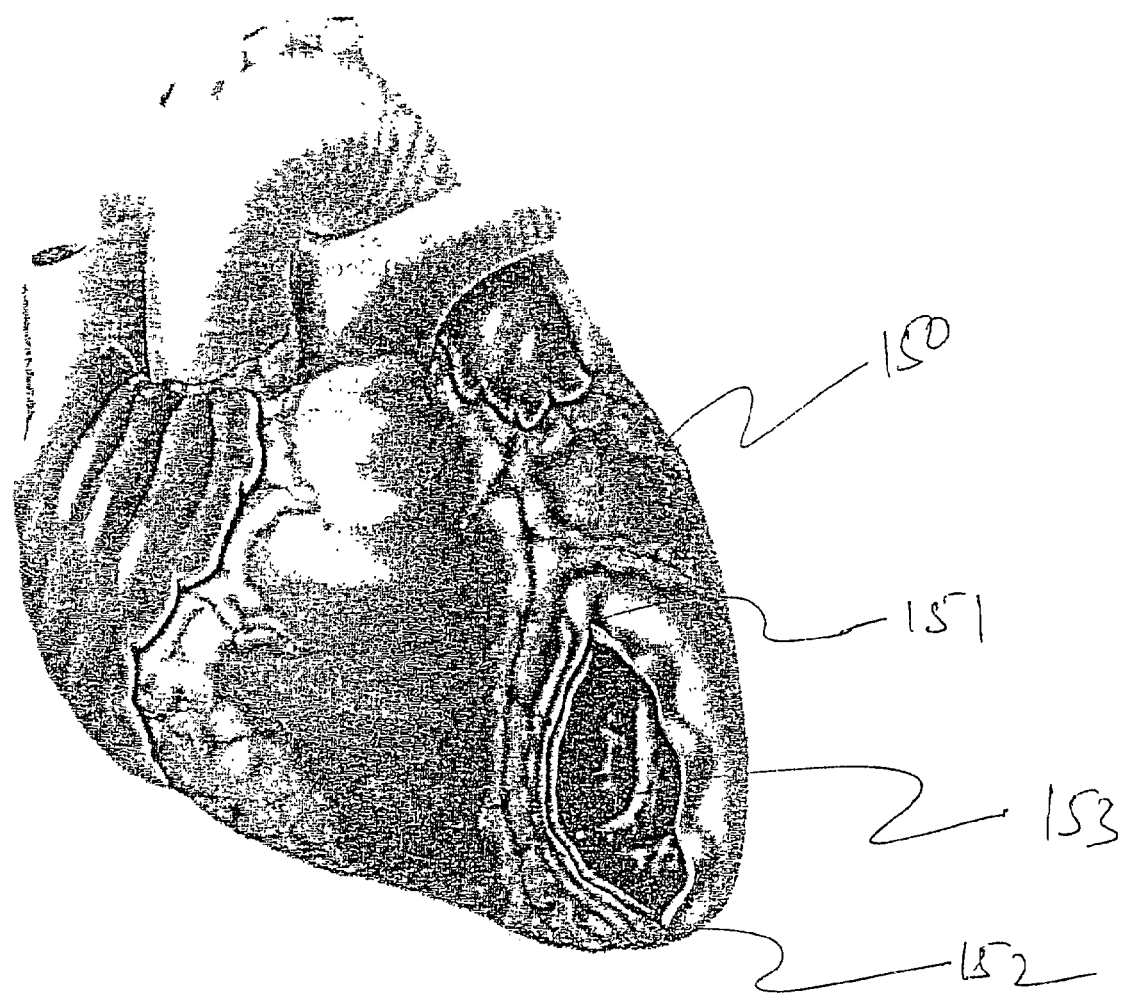
FIG. 12A: Illustrates an embodiment of making an incision into a heart.
Figure 12B:
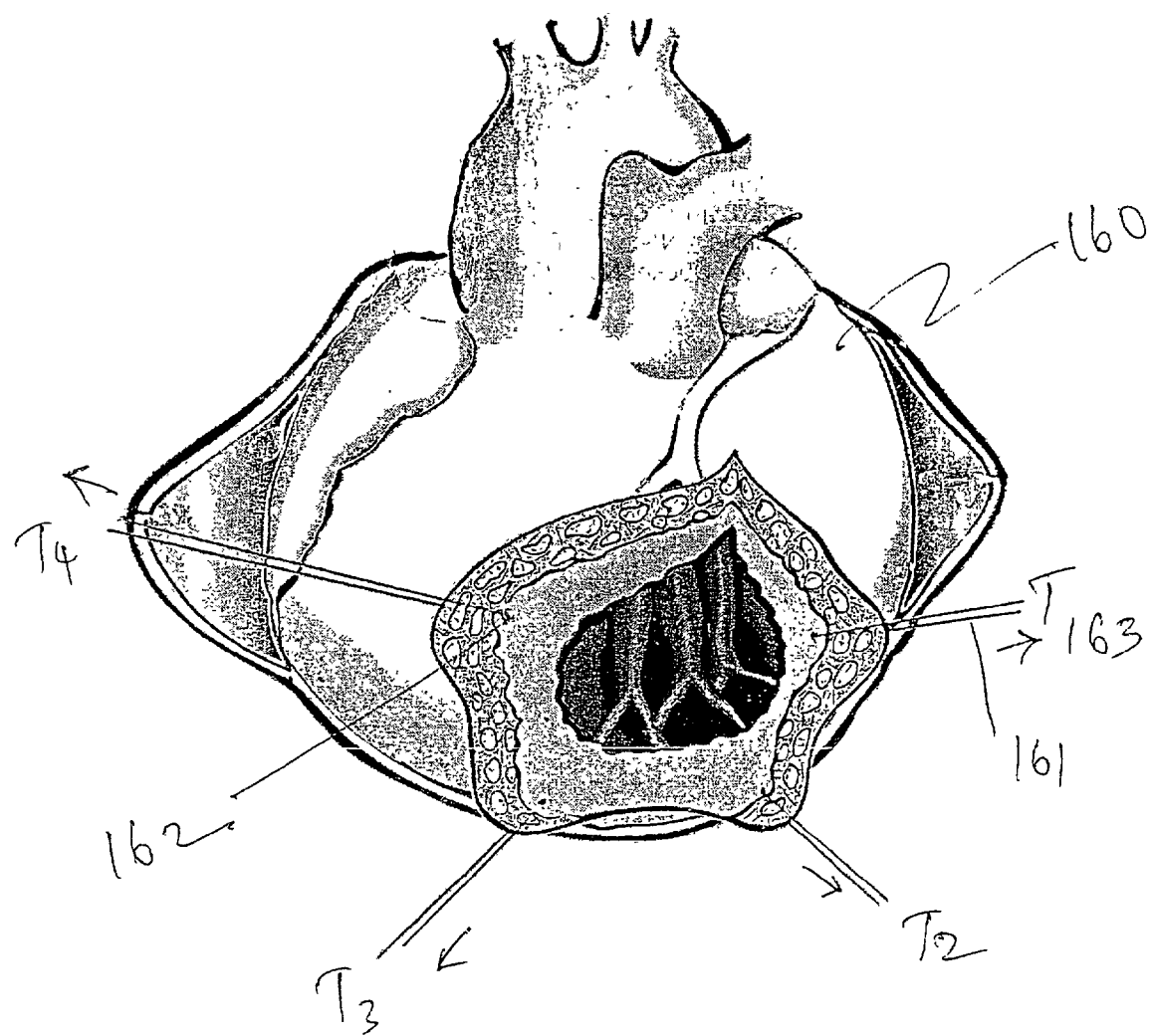
FIG. 12B: Illustrates an embodiment of placing sutures and opening an incision in a ventricle.
Figure 12C:
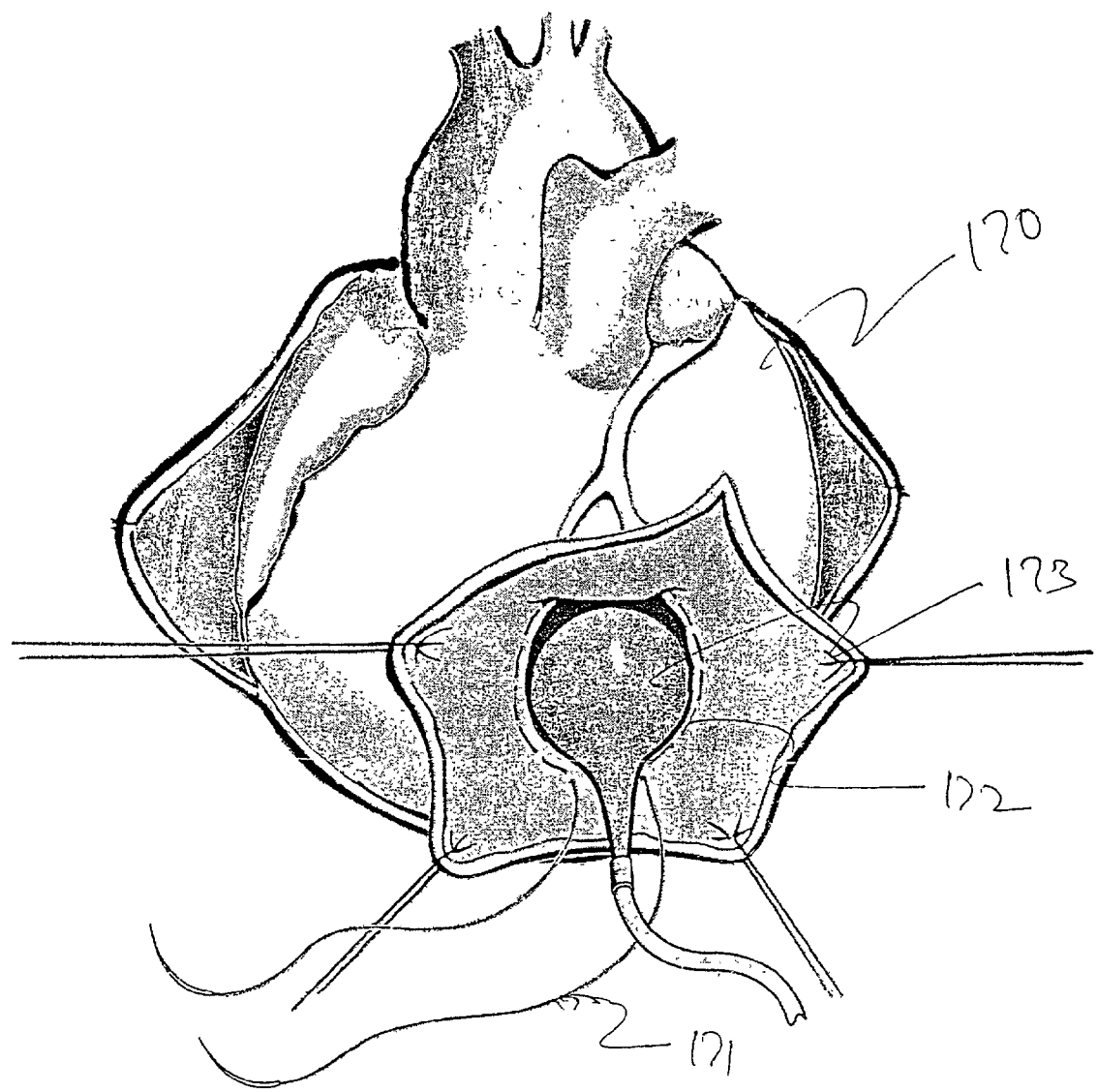
FIG. 12C: Illustrates an embodiment of a sizing and shaping device in a ventricle.

Methods and apparatus of various embodiments will be described generally with reference to the drawings for the purpose of illustrating the particular embodiments only, and not for purposes of limiting the same. The illustrated embodiments address the ability of the doctor to accurately assess the effects of cardiac disease on an individual patient and to use an appropriate treatment to restore the cardiac system to its optimal or best acceptable condition. In one embodiment, this is accomplished by using an analytical tool that takes images of the patient's own heart as in FIGS. 5A, 5B and other data and converts them to a multi-dimensional finite element model, such as illustrated in FIG. 10. The multi-dimensional finite element model may interact and respond to other models or a set of models. The model of the heart FIG. 10 may also be connected to a model of the circulatory system and/or a model of the cardiac system. These models may simulate the performance of the heart and/or its effect on the circulatory system. This is a procedure that determines the appropriate areas to be repaired and/or replaced or otherwise medically treated for each individual patient uniquely. The procedure may determine the effects that the treatment may have on the structural element treated, the other structural elements of the heart, and/or on the entire heart.

One embodiment is a system and method for capturing the geometry of the heart and its components using imaging technologies. Examples of imaging technologies may include, but are not limited to, MRI imaging, echocardiography, or PET. Turning now to FIG. 1, in 10 patient data is acquired. Some other factors and information that may be captured include:

a. Myocardial stiffness
b. Ventricle wall thickness
c. Heart rate
d. Ventricle wall tension
e. Right and left ventricle volumes
f. Mitral Valve Annulus
g. Chordae Tendinaea
h. Papillary Muscles
i. Mitral Valve Leaflets
j. Ventricle Endocardium Border
k. Ventricle Epicardium Border
l. Aortic valve annulus
m. Aortic valve cusps
n. Tricuspid valve apparatus
o. Pulmonary valve apparatus
p. Ventricle wall thickness
q. Ventricles areas of akinesia
r. Ventricle areas of dyskinesia
s. Ventricle areas of asynergy
t. Ventricle preload
u. Ventricle filling pressure
v. Heart's arterial system
w. Heart's flow through the arterial system
x. Heart's venous system
y. Left and right atrium volumes
z. Left and right atrium wall thickness Some or all of these factors may be used to create a multi-dimensional finite element computer model of a heart (11). One example of a multi-dimensional model is a three-dimensional model that displays not only the three dimensions of a geometry of a heart but may also depict this geometry as it changes over time. In an embodiment, a dimension may include physiological factors. An example of a physiological factor dimension may include heart production of a hormone B-type natriuretic peptide in reaction to increased wall stress. Production of a hormone could serve as a dimension to a model. In an embodiment, software producing a model may run on a personal computer type of machine, it may run at a central location, and/or it may be processed at one location and delivered to another location. A four dimensional model may allow a doctor to visually inspect the status of all the elements of a heart. A model may be used to determine a variety of information, either pre-treatment, during the treatment and/or post-treatment, including, but not limited to:

a. The areas of the mitral, aortic, tricuspid or pulmonary valves that may need to be repaired or replaced and what affect each repair may have on the other components.

b. What vessels are blocked and may need to be grafted, where to graft and what effect the revascularized muscle may have on the other components.

c. What areas of the ventricle are akinetic, dyskinetic or hibernating, to show what areas may be excluded during ventricular restoration and what effect the exclusion may have on the other components and aspects of the ventricle and heart.

d. How a patient's heart may respond to medication treatment.

e. The effects of placement of a corecap restraining device, Myosplint shape changing device or other device on the outside of the ventricle may effect the heart.

f. The effects of chordae length adjustment or papillary base relocation may effect the heart.

g. The effects of placement of any ventricular assist device may have on the heart.

h. The vessels that are blocked and may need to be stented, where to stent and what affect the revascularized muscle may have on the other components.

A model may allow a user (e.g., a doctor) to select a treatment option (12) and allow the doctor to manipulate the image and model (13). A model may analyze what effects his virtual treatment may likely have on the cardiac geometry (14). A model may calculate predicted outcomes based on physiology and hemodynamics (16). A model may display the potential clinical outcomes to the doctor (17). The potential outcomes display may be, but are not limited to, the following:

a. The estimated performance of the valves and ventricle after the procedure; i.e. regurgitation, reduced flow across the valves, ejection fraction etc.

b. The flow through the grafts or stents and what areas of the myocardium the grafts or stents may perfuse.

c. The volume and contractile state of the ventricle after excluding tissue.
d. The positioning and performance of the valve apparatuses after reconstruction of the ventricle.
e. The effects that a drug or combination of drugs may have on the entire heart.

In an embodiment, a doctor may be able to select a displayed intervention (18), try another treatment, and/or modify the current intervention (19) and the cycle may repeat itself. When the doctor accepts the potential clinical outcomes, the model may produce the specifications for the intervention (20). These specifications may lead to the development of a template, tools, and/or devices to guide the doctor in translating the virtual intervention on the model to the actual intervention on the heart (21). In some cases templates, tools, and/or devices may not be needed to perform the intervention and specifications such as the length of a chordae tendinae may be sufficient output from the model to allow the doctor to perform the intervention. Additional devices may be generated from the models to help the doctor implement the procedure that the model may have predicted to provide the best outcome. Use of some or all of above listed factors may be used to evaluate post-treatment of the condition of the patient. A database of surgical pathologies, treatments and outcomes may be gathered, maintained and analyzed to further refine the treatment of cardiac diseases and disorders.

FIG. 1 describes a method and apparatus for performing cardiac valve correction planning. The procedure acquires imaging information, such as, but not limited to, MRI, PET or echocardiography imaging data of the patient's ventricle (10). These imaging systems are common in most hospitals and the leading manufacturers of these systems are General Electric, Siemens and Phillips. Other information such as, but not limited to, stiffness, wall thickness, heart rate, wall tension, right ventricle volume, valve apparatus locations, epicardium borders, and/or endocardium borders may be needed to convert the data to a multi dimensional model of the heart.

Figure 9:
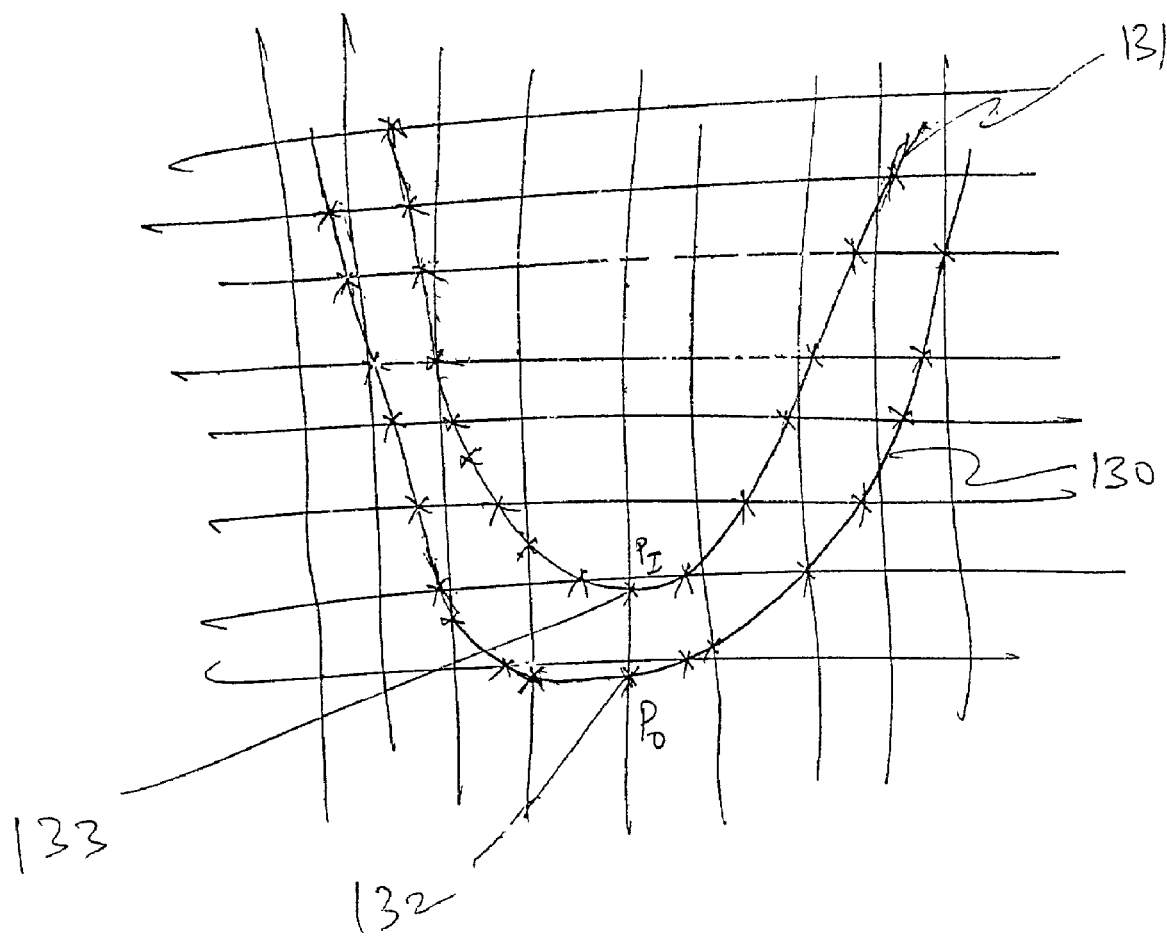
FIG. 9: Illustrates an embodiment of a model created from MRI images.

In some embodiments, imaging data is often acquired as sectional views (FIGS. 5A, 5B). One way of combining sectional views and converting them into a model may be done by overlaying the sectional view on a XY grid. FIG. 9 shows a diastole picture of the heart in a long axis along plane AA with the grid superimposed. The points of intersection of endocardium (and epicardium) with the grid are identified in XY coordinates. Similarly XY coordinates are identified on all the planes. Since the angular relationship between each plane is known (angle θ, in FIG. 5A), all the data points may be converted into XYZ coordinates. The boundary layer generated by connecting the internal point $P_{I1,2,3}$ . . . defines the endocardial boundary, and the boundary layer generated by connecting the external points $P_{O1,2,3}$ . . . defines the epicardial boundary. This defines the heart in a three dimensional space. Once the three dimensional model is created the time frame of the cardiac over which all the images were made may be added to show the heart move in time during its cardiac cycle (four dimensional model).

In an embodiment, once the multi dimensional object is defined, it may be converted to elements of a finite element model and a finite element mesh that represent a heart and its components to create the model (FIG. 10). Some of the components of the heart that may be identified as different structural elements of a finite element model are listed below, but the apparatus and method is not limited to these components;

a. Mitral valve annulus FIG. 11a
b. Mitral valve leaflets FIG. 11b
c. Chordae Tendinae FIG. 11c
d. Papillary muscles FIG. 11d
e. Aortic valve with cusps FIG. 11e
f. Left ventricle outflow tract FIG. 11f
g. Left ventricle walls FIG. 11g
h. Septum FIG. 11h
i. Myocardium of the heart FIG. 11i
j. Left atrium FIG. 11j
k. Ascending aorta FIG. 11k In an embodiment, elements of a heart may have different structural properties. The structural properties of myocardium and other cardiac structures may be obtained from various sources in literature, for example, the properties of the ventricle myocardium may be found in, J. M. Guccione et. al., "Passive Material Properties of Intact Ventricular Myocardium Determined from a Cylindrical Model", Journal of Biomechanical Engineering Vol. 113, February 1991. Once all the structures are geometrically defined and structural properties are known, a finite element model may be created. A method of converting a defined object to a finite element mesh is describes in U.S. Pat. No. 5,892,515, and is hereby incorporated by reference. "Finite element analysis" is a mathematical approach to solving large (complex) problems. Generally the subject is segmented or discretized into many pieces that have closed form solutions. That is, each piece is definable by a linear equation, and hence is a "finite element". Collectively, the linear equations of the pieces form a system of equations that are simultaneously solvable. Computer programs for simulating finite element analysis in various applications exist; for example, design engineers use finite modeling programs. Typically many thousands of elements are created to model a subject object and in particular three-dimensional objects. For each element, there is geometric information such as an (x, y, z) coordinate at a point in the element, an element type, material property, stress value, displacement, thermal value, etc. Such information is definable by linear equations for the elements. Finite analysis may be employed to model the subject object. Examples of finite modeling programs include: ABAQUS by Hibbitt, Karlsson, and Sorensen, Inc. of Pawtucket, R.I., ANSYS by Swanson Analysis Systems Inc. of Houston, Pa.: SUPERTAB by Structural Dynamics Research corp. of Ohio; and PATRAN by PDA Engineering of Costa Mesa, Calif.

In an embodiment, once a finite element model has been created, an image of a heart and/or some of its structural elements may appear on a monitor to allow a doctor to interact with the model. An image of a heart, as illustrated in FIG. 10, may be displayed. Relevant data on the state of the heart, for example left ventricle volume, blood pressure, ejection fraction, heart rate, may also be displayed. The image may be interactively connected to the model (11) to allow the doctor to simulate the effects of the treatment before it is administered. For example, a pull down menu that is commonly used in many software applications like word processing software or CAD software may be accessed to select the type of treatment desired (12) (e.g., surgical ventricular repair, bypass grafting, mitral valve repair etc.). For example, a doctor may select the mitral valve option to shorten the chordae tendinae or tighten the mitral annulus. In the chordae tendinae example, the model may separate the chordae elements from the entire model and present it to the doctor, to allow the doctor to interact with the elements. Interaction may come in various forms. A pull down menu standard to most software programs could present the doctor with a list of options, such as selecting the type of scalpel to use, the type of suture material etc. The physical characteristics of these implements may be entered into a database (22) that the model may access. Once the doctor has selected the implement to use a box or another pull down menu may appear asking for further information on how to use the implement. For example, with a scalpel the box will ask the doctor how long and how deep he wants to make the incision. The doctor will then be asked to identify by clicking with a mouse or stylus the start and end points of the incision. When the requested information has been entered, an incision may appear on the model corresponding to the input of the doctor and sized appropriately for the heart according to the characteristics of myocardium etc. that are built into the finite element model (14). Methods to model the physical properties of the heart exist to create the manipulation portion of the model. A method to create a finite element model of the heart is written about by K. D. Costa et. al., "A Three-Dimensional Finite Element Method for Large Elastic Deformations of Ventricular Myocardium: I-Cylindrical and Spherical Polar Coordinates, Journal of Biomechanical Engineering, November 1996, Vol. 118 pp. 452-463. The physical properties of the elements of the heart on which to base the finite element equations for the structural elements may be found in, Hunter P. J., et. al., "Modeling the mechanical properties of cardiac muscle", Progress in Biophysics & Molecular Biology 69 (1998) pp. 289-331. Modeling the diseased areas of the left ventricle has been described in Rez Mazhari, et. al., "Integrative Models for Understanding the Structural Basis of Regional Mechanical Dysfunction in Ischemic Myocardium", Annals of Biomedical Engineering, Vol. 28, pp. 979-2000. The properties of the ventricle myocardium may be found in, J. M. Guccione et. al., "Passive Material Properties of Intact Ventricular Myocardium Determined from a Cylindrical Model, Journal of Biomechanical Engineering Vol. 113, February 1991. Once the doctor has shortened the chordae the model presents the image of the new shorter element and presents an image of the other elements with the effect that the shortening of the chordae has had on them along with clinical outcomes (16)(17). The doctor may save the results of the first intervention and repeat the procedure in a different manner (19) to compare the outcomes of different interventions. The doctor may then select the optimal outcomes (18) and perform the procedure in that manner. Optimal outcomes may be based on a variety of cardiac performance parameters. They may include, ejection fraction, end systolic volume, stroke volume index, cardiac output, mitral regurgitation, pulmonary artery pressure, mean arterial pressure, percentage of asynergy etc. Optimal outcomes are very doctor dependent, some doctors may prefer higher ejection fraction and may be willing to tolerate slight mitral regurgitation. Other doctors will tolerate no mitral regurgitation and accept a lower ejection fraction to achieve no regurgitation through the mitral valve. When the doctor is satisfied that the intervention is the optimal possible for this patient, he accepts the intervention and the model may produce specifications to assist the doctor in performing the intervention (20). Specifications may be simply a display of the final length of the chordae. In more complicated procedures specifications may result in the production of patient specific devices, which will assist the doctor with translating the virtual intervention to an actual intervention on the patient. Patient specific devices may be simple variations to the existing devices like customized annuloplasty ring and/or they may be more complex devices like prosthetic mitral apparatus. With the information provided by the model the doctor may proceed with the intervention with greater assurance that the result will be the optimal possible (21).

Figure 14A:
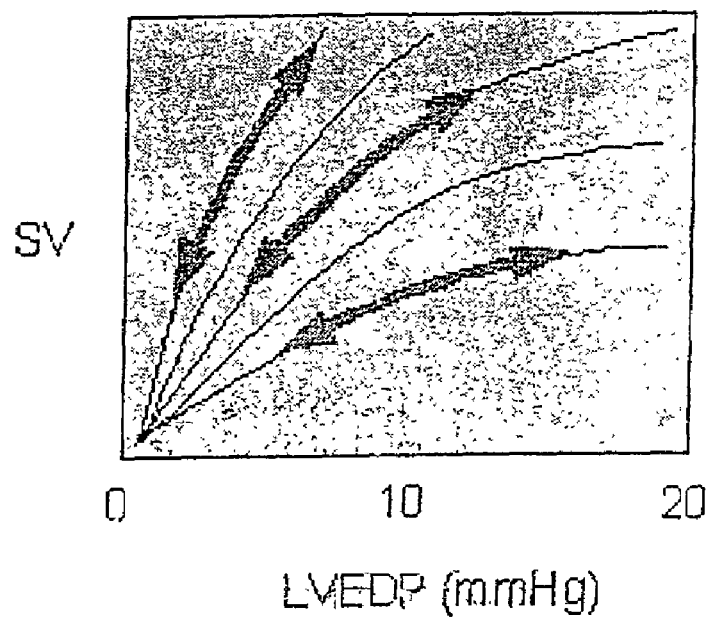
FIG. 14A: Illustrates an embodiment of a Frank-Starling curve.
Figure 14B:
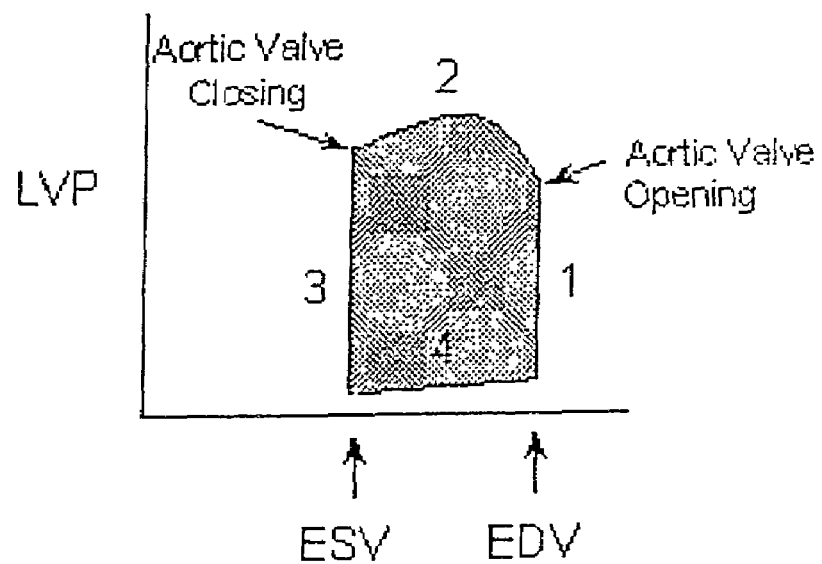
FIG. 14B: Illustrates an embodiment of pressure volume loops.

In an embodiment, separate model or models may be able to determine the clinical outcomes of the procedure. For example physiological and hemodynamic conditions of the heart may be modeled. The physiological properties of the heart are well understood, the Frank-Starling curve and the law of Laplace etc., and are written about in numerous publications to include Hurst et. al., Hurst's The Heart, McGraw-Hill, 1998, excerpts are depicted in FIGS. 14A, 14B. Frank Starling curve varies from heart to heart based on various factors, like contractility, wall stress, sphericity index, diseased state etc. The curve that best matches a given patient may be obtained by comparing the patient specific characteristics to those of other patients in a CHF database 33 (FIG. 2).

Figure 15A:
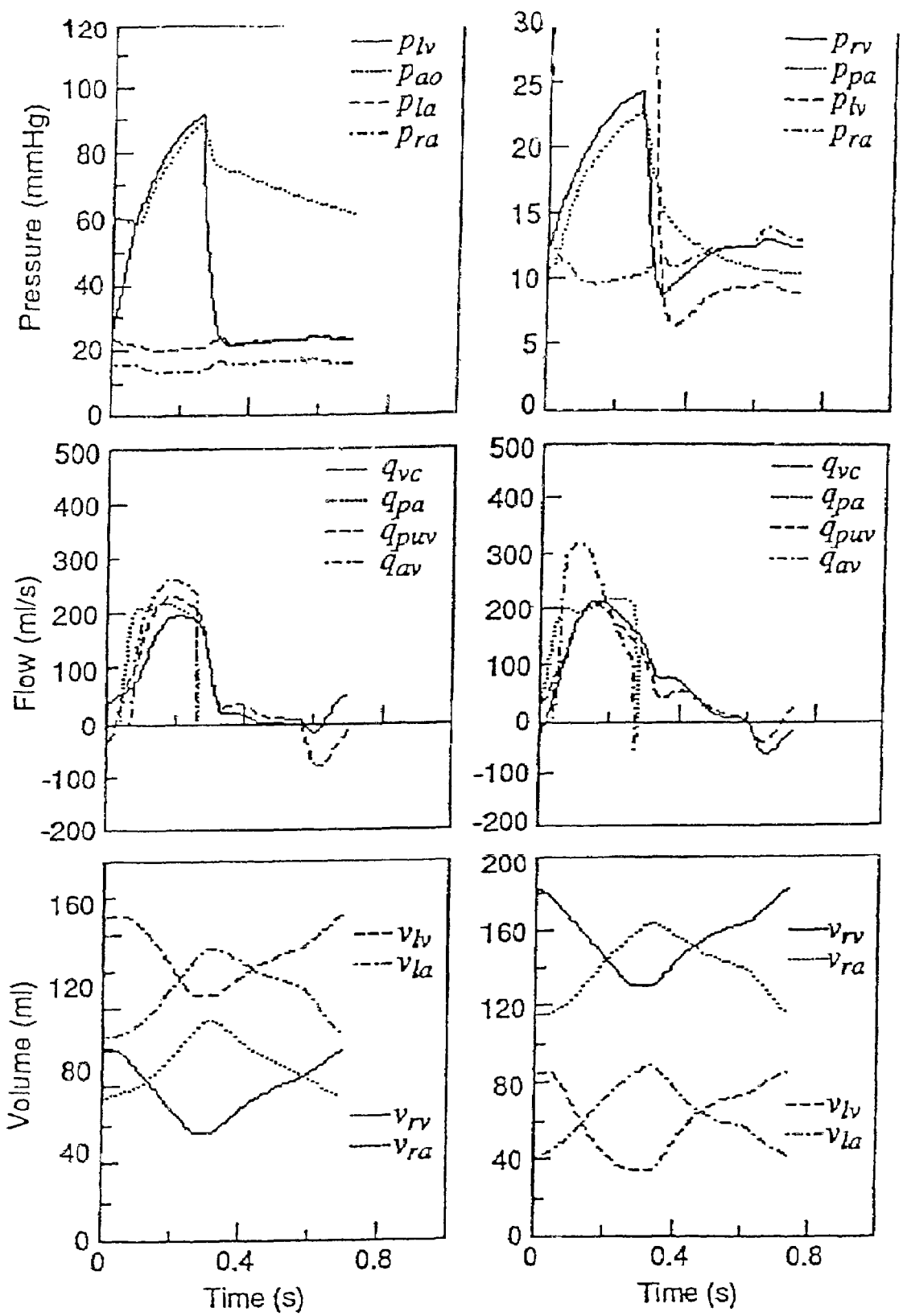
FIG. 15A: Illustrates an embodiment of outputs from a hemodynamic model of a heart and circulatory system by Professor Ying Sun, of The University of Rhode Island.
Figure 16:
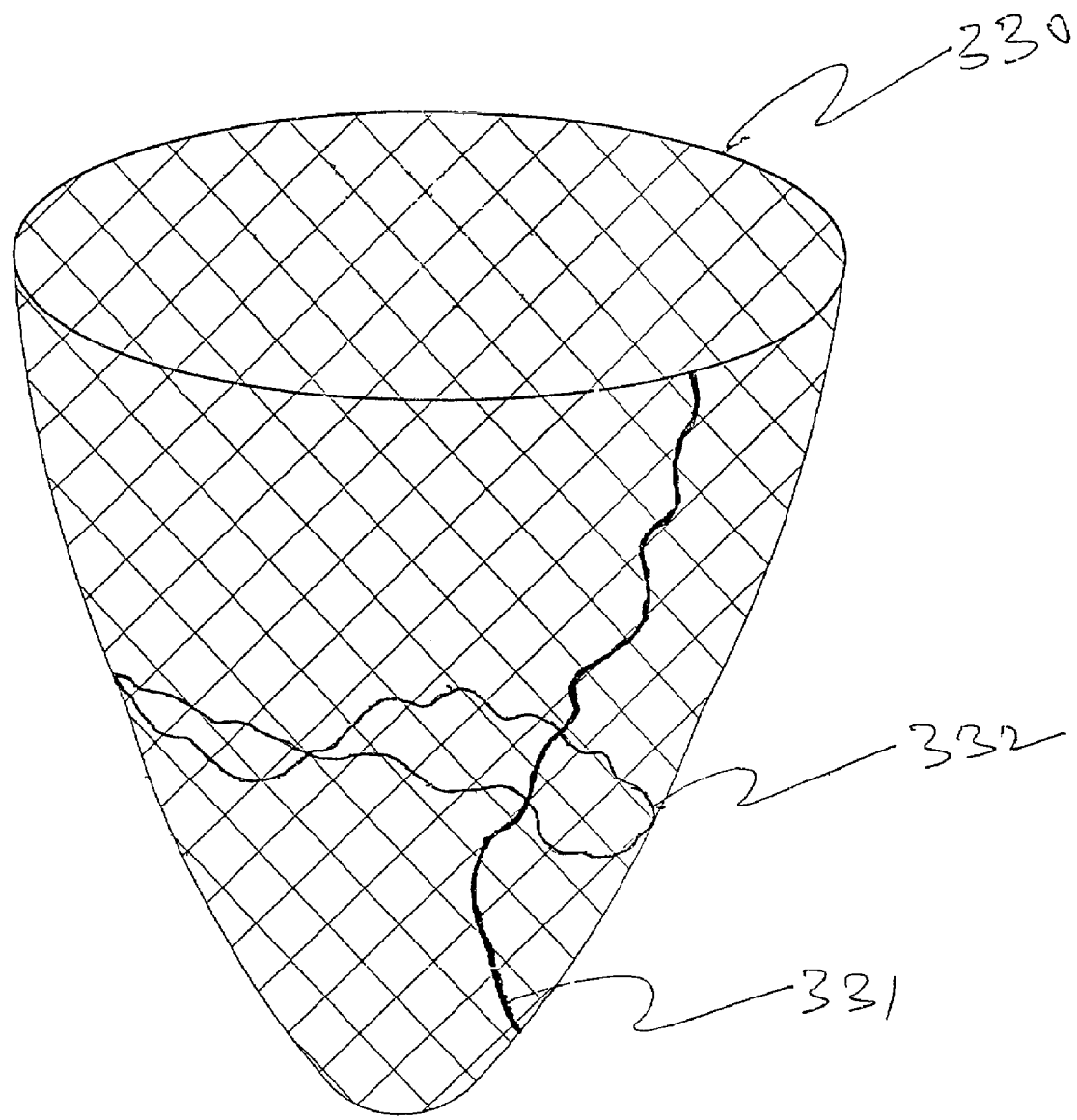
FIG. 16: Illustrates an embodiment of a mesh that has anatomical landmarks of a heart and a location of a diseased tissue superimposed on it.

A hemodynamic model has been developed and published by Professor Ying Sun, et. al., "A comprehensive model for right-left heart interaction under the influence of pericardium and baroreflex, The American Journal of Physiology, 1997, pp. H1499-H1514, FIG. 15A. In an embodiment, these two models may interact with the finite element model to show the doctor what effect his interaction has had on the other elements and the whole heart. The physiological models may vary from very simple such as an equation of a curve of Stroke Volume vs. End Diastolic Volume as in the Frank-Starling curve, to much more complicated computational biology models. The hemodynamic models may vary from simple models of the pressure drop vs. flow relationship to complex computational flow dynamics like the one published by Makhijani et. al. "Three-dimensional coupled fluid—Structure simulation of pericardial bioprosthetic aortic valve function" ASAIO Journal 1997; 43:M387-M392.

Figure 13A:
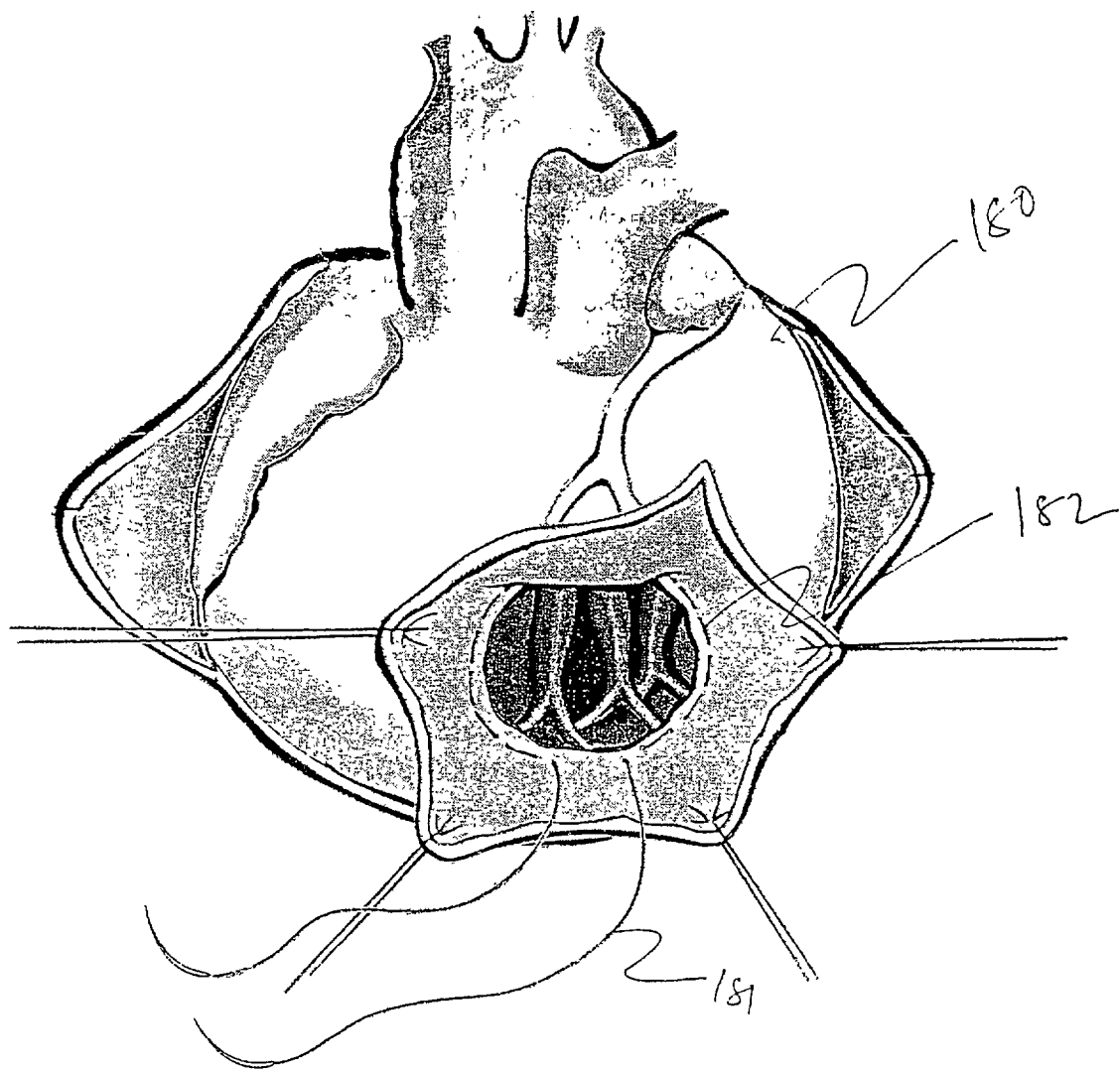
FIG. 13A: Illustrates an embodiment of a Fontan Stitch—creation of neck for placement of a patch (FIG. 13L shows one embodiment with patch).
Figure 13B:
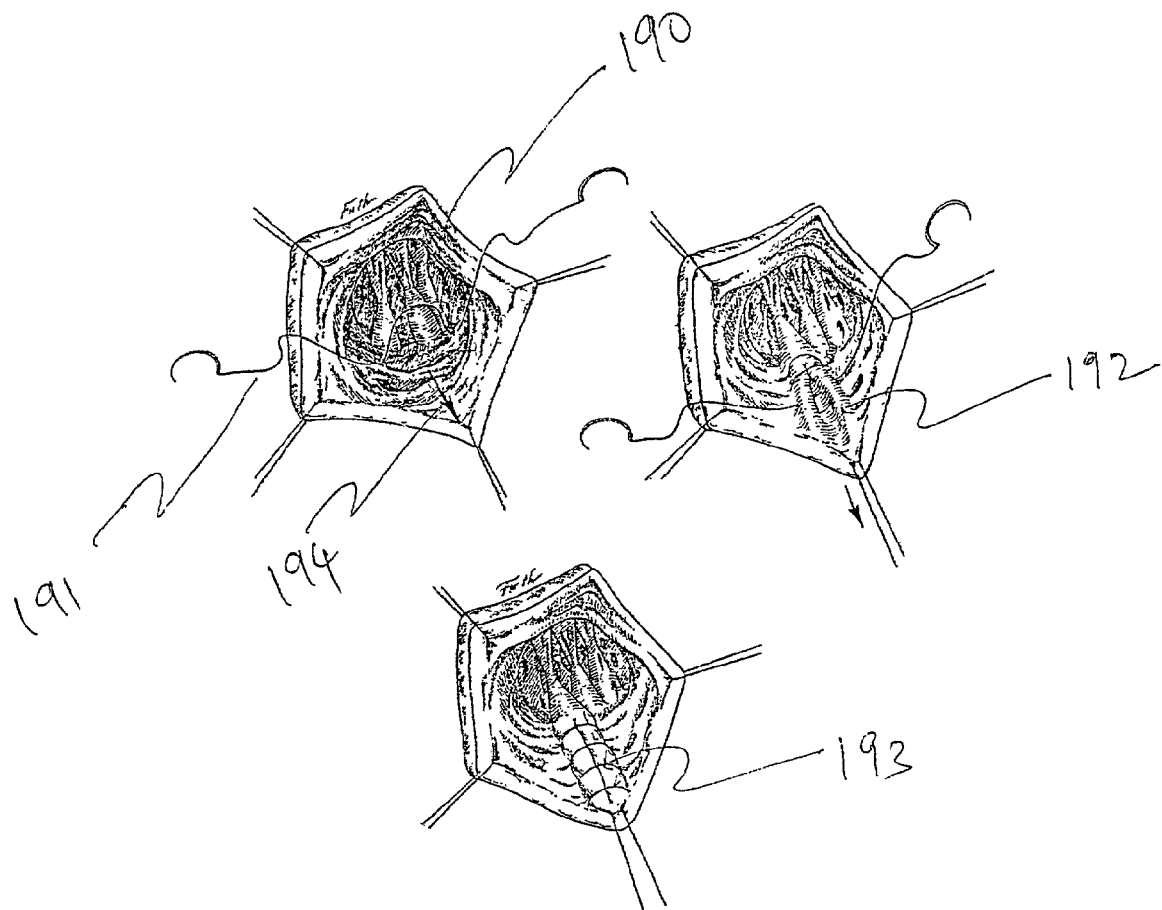
FIG. 13B: Illustrates an embodiment of suture placement to imbricate stretched tissue.
Figure 13C:
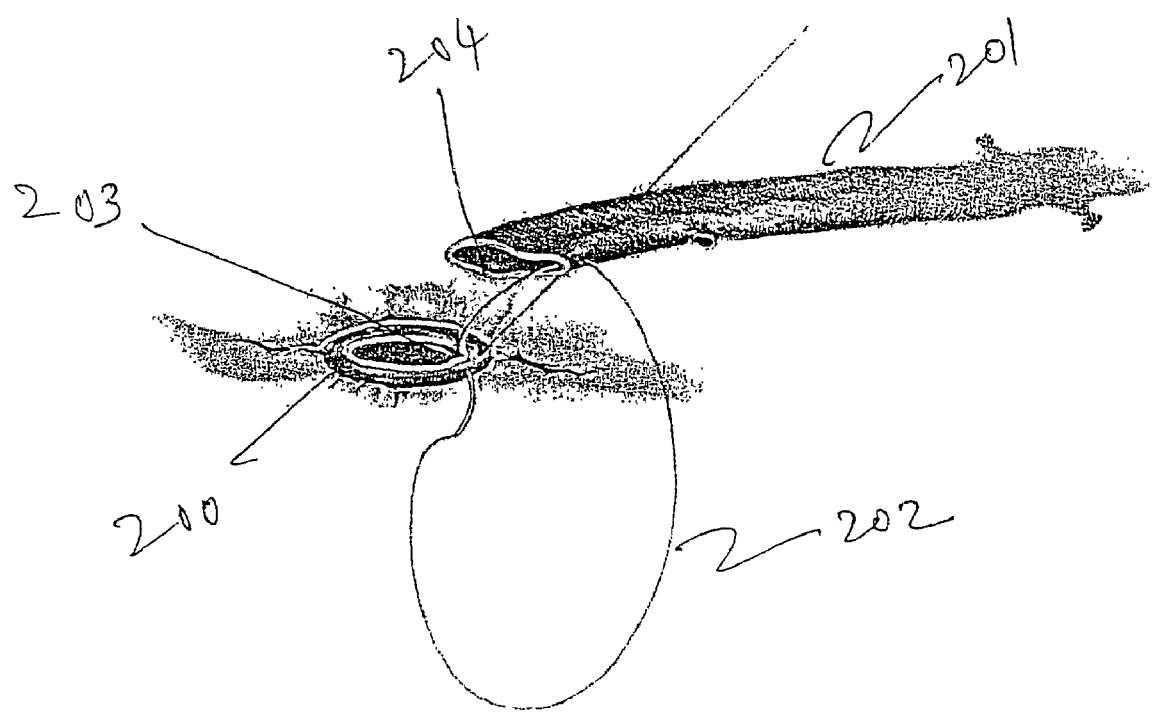
FIG. 13C: Illustrates one embodiment of anastomosis.
Figure 12E:
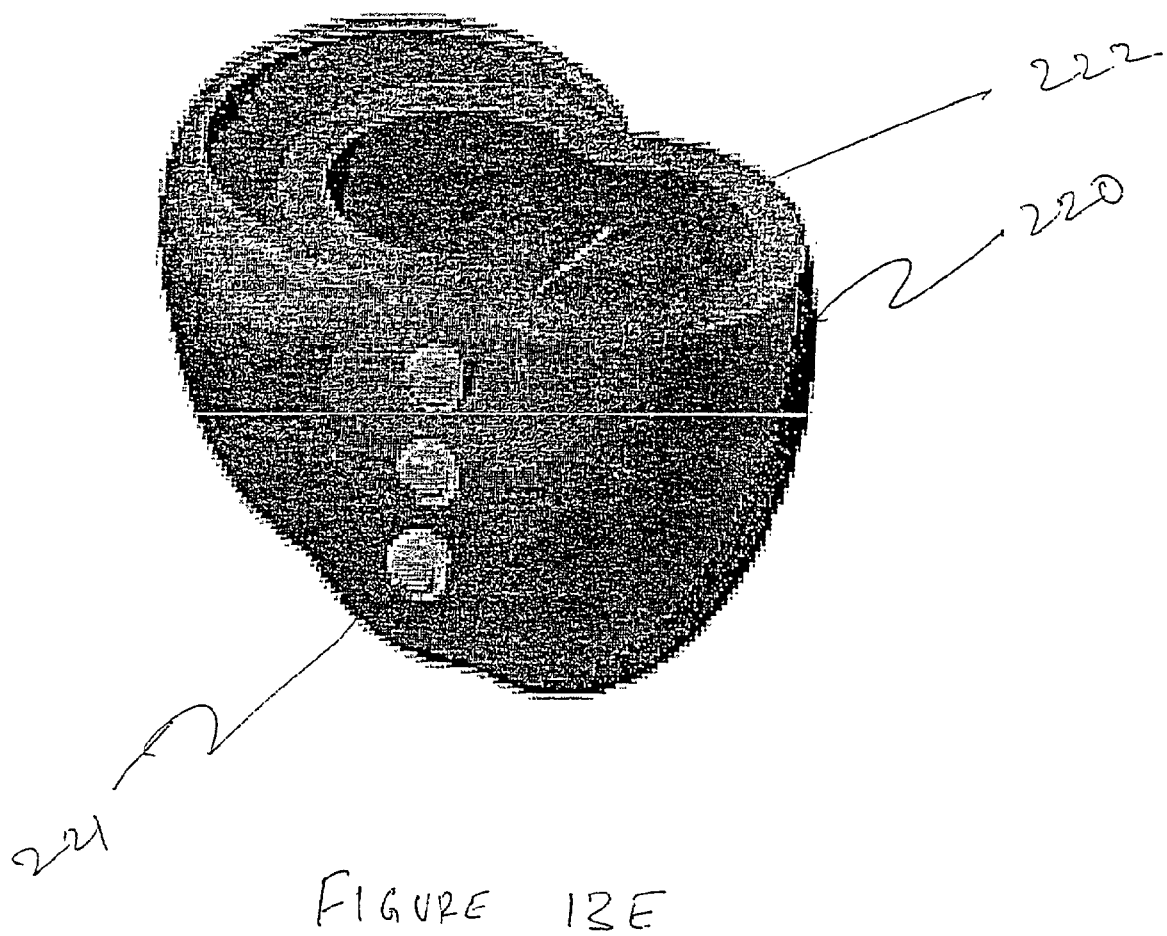

In an embodiment, placement of an annuloplasty ring may be simulated to show its effect on the annulus, connected tissue and ventricle, FIG. 13D. A patient's heart may be imaged (10). The image may be converted to a finite element model (11). Software may allow a doctor to select the type of treatment desired (12) and/or access a database to select the device to be used (22), in this case an annuloplasty ring. The model may then display to the doctor the mitral valve and allow him to instruct the model on where to place the ring, which suture to use in securing the ring, how much tension to put on the sutures, and/or distance between each bite etc (13). The model may then apply this intervention to the mitral valve annulus and the other elements of the mitral valve and the other components of the ventricle and the heart as a whole (14). Other data, if necessary, is pulled into the equation (15) if needed. The model may recreate the image on the monitor to show the doctor the effects of his interaction (16). The potential clinical outcomes (17) may be determined by the model through interaction with the physiological and hemodynamic models FIG. 15A: Hemodynamics for left heart failure (graphs on the left) and Right heart failure (graphs on the right). $P_{lv}$—left ventricular pressure, $p_{ao}$—Aortic pressure, $p_{la}$—Left atrial pressure, $p_{ra}$—right atrial pressure, $p_{rv}$—right ventricular pressure, $p_{pa}$—pulmonary arterial pressure, $p_{ra}$—right atrial pressure, $q_{vc}$—flow through venacava, $q_{pa}$—flow through aortic valve, $v_{lv}$—volumen of left ventricle, $v_{la}$—volume of left atrium, $v_{rv}$—volume of right ventricle, $v_{ra}$—Volume of right atrium. This simulation may show the ring's effect on the size and orientation of the annulus as well as the effect the ring may have on the connected tissue, i.e. does it affect the length of the chordae tendinae, shape of the ventricle, etc. The model may be analyzed to show the surface area of the opening of the shortened annulus, how much flow may come through that opening and how the change in flow may affect the ventricle. The model may predict if there is a mitral valve prolapse. A database of medical devices (e.g., medical devices depicted in FIGS. 13C, 13D, 13E, 13G, 13H) may be created and accessed to allow the simulation of these devices. Medical devices may be tested for physical properties and these physical properties encoded into a finite element model, as has been done for elements of the heart described above. The finite element models for the devices are stored in the database (22) and accessed by the doctor by selecting the object by, for example, its common name. For example, prosthetic valves and prosthetic valve apparatus (mechanical and bioprosthetic) may be called upon to place different artificial valves into the heart. Performance of the heart with the different valves may be assessed to select the correct valve for the patient. The model might also give estimated values of post-surgery performance of the heart. The model might display estimated ejection fraction, regurgitation, sphericity of ventricle, volume of the ventricle, percentage of shortening on the long and short axis, and maximum and minimum flows across the valves, tension in chordae etc. In some instances, it is likely that off the shelf devices do not provide optimum results. For example the annuloplasty rings comes in various sizes, it is likely that for a given patient when a smaller size is used it may end up creating more than acceptable tension in the chordae, while going to next size up may lead to mitral insufficiency. In such situations, the model may come up with a specification for the ring that falls between those two sizes, which offers the best possible outcome for that patient.

Figure 2:
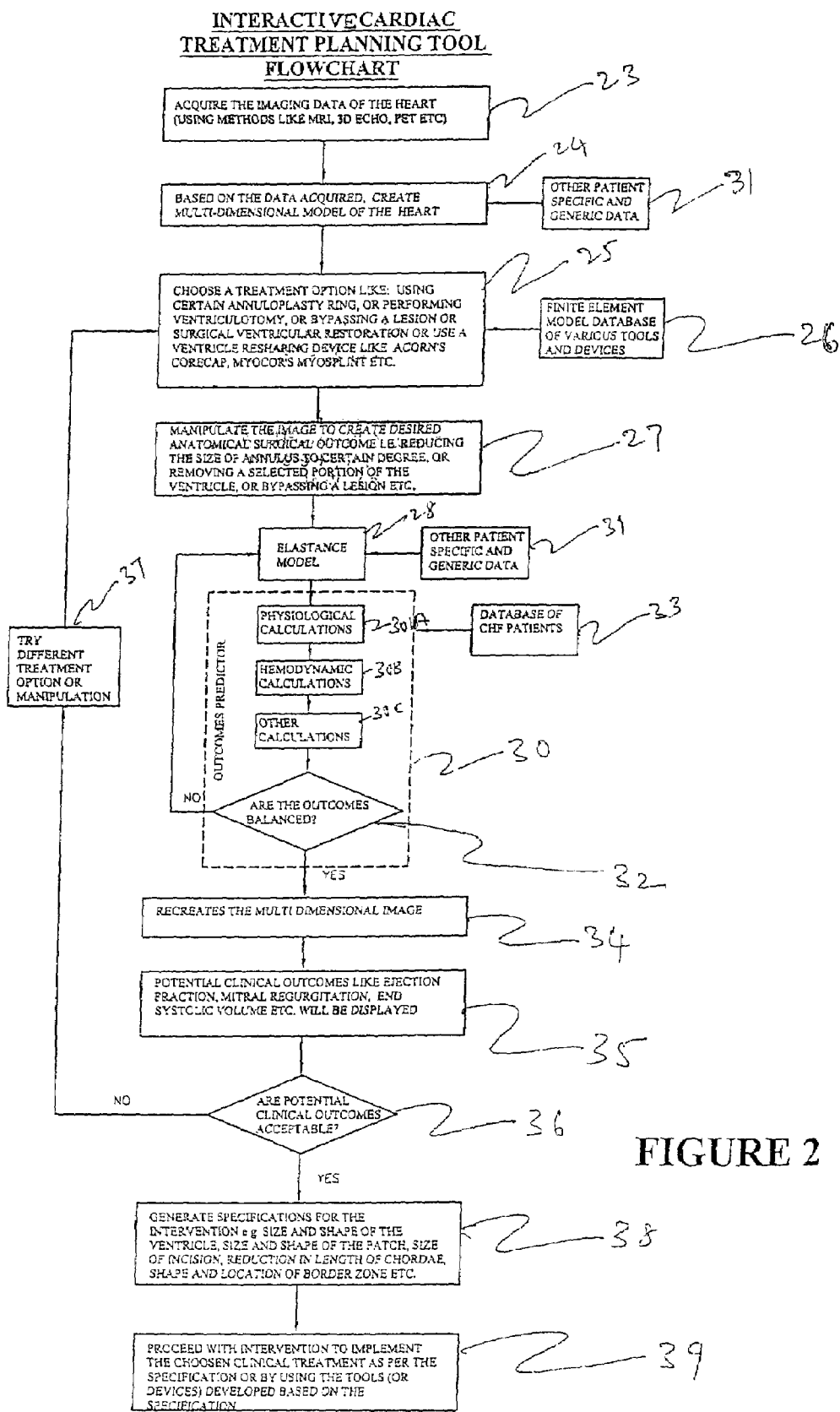
FIG. 2 is a flowchart illustrating one embodiment of a method of a cardiac intervention.
Figure 13F:
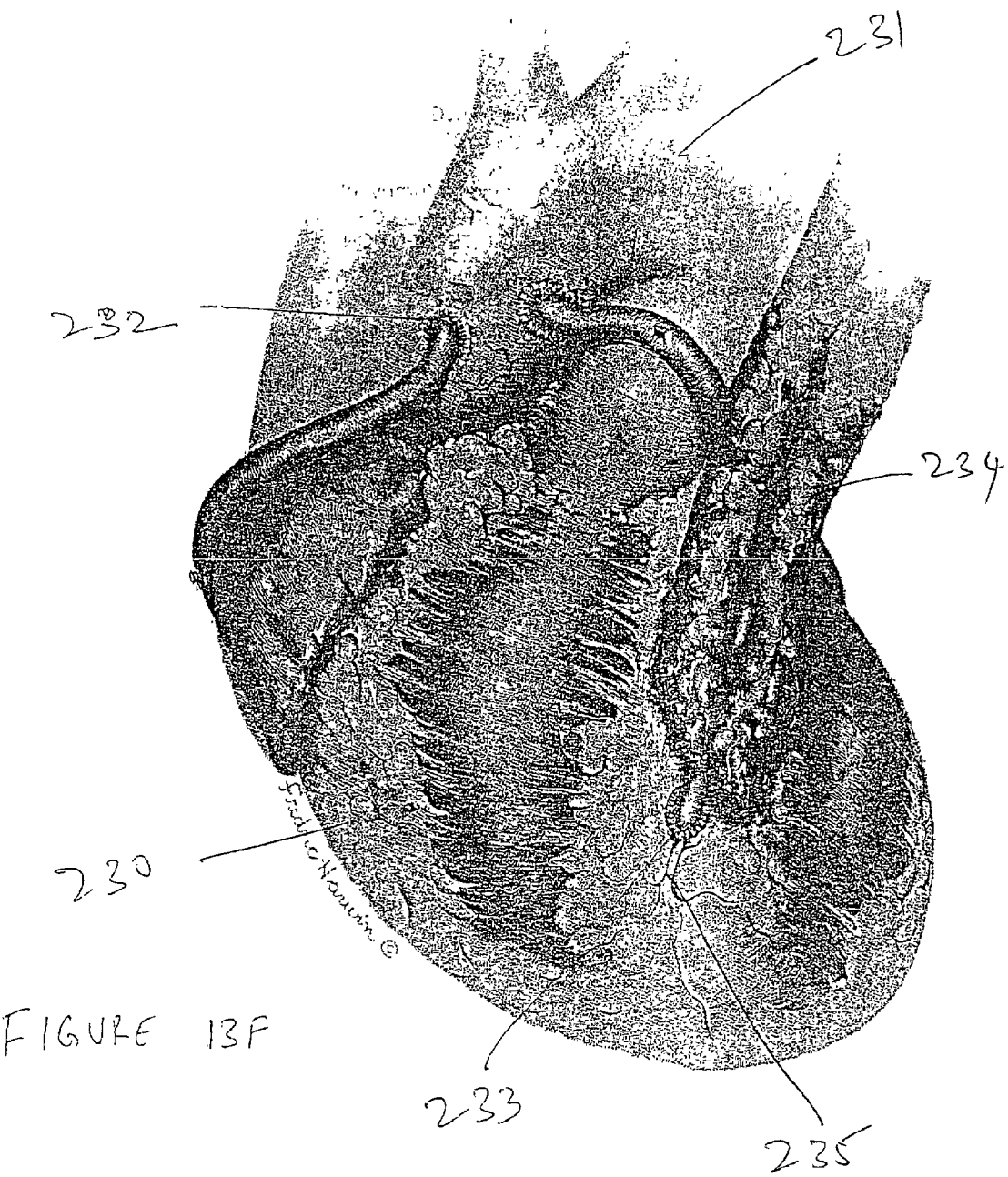
FIG. 13F: Illustrates an embodiment of completed bypass grafts.
Figure 13:
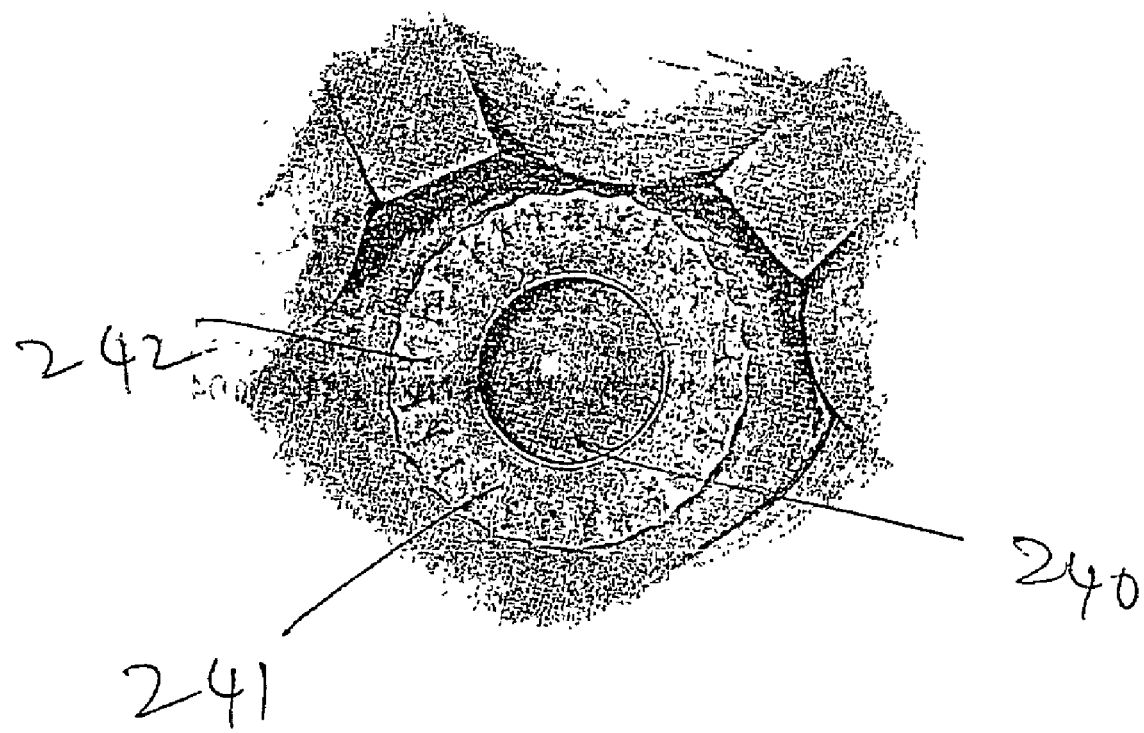
FIG. 13D: Illustrates an embodiment of a Mitral Valve with an insufficiency and a Valve after it is corrected with an annuloplasty ring.
FIG. 13E: Illustrates an embodiment of a placement of a Myocor splint.
FIG. 13G: Illustrates an embodiment of a mechanical heart valve.
FIG. 13H: Illustrates an embodiment of an Acorn Corcap.
FIG. 13I: Illustrates an embodiment of a linear closure of an opening.
FIG. 13J: Illustrates an embodiment of a buttress suture.
FIG. 13K: Illustrates an embodiment of reforming a ventricle to give a new volume.
FIG. 13L: Illustrates an embodiment of placement of a patch to close an opening in a ventricle.
FIG. 13M: Illustrates an embodiment of tightening a mitral annulus with a suture.
FIG. 13N: Illustrates an embodiment of replacing an aortic valve.
FIG. 13O: Illustrates an embodiment of repairing a mitral valve—excising a portion and regrafting the leaflets.

In an embodiment, FIG. 2 depicts a method and apparatus for treating cardiac disease. Images of a ventricle are taken (23) and a finite element mesh model is created of the ventricle and of the structural elements as described previously (24). The doctor chooses a treatment option (25), e.g., surgical ventricular repair. The doctor using pull down menus, or another standard interactive means chooses the implements that are needed to perform the procedure (26). The doctor may perform the treatment by interacting with the image and/or the model (27). Interacting with the model, the doctor may for example select a scalpel and identify where and how to incise the ventricle. He then identifies the tissue he wants to exclude and places a Fontan stitch (depicted in FIG. 13A). When the doctor excludes tissue the model eliminates the sections of the finite model that correspond to this area from the calculations of the ventricle parameters and outcomes. The model may keep these elements solely as graphical depictions. The model may try various degrees of volume reduction of the ventricle (depicted in FIG. 13K) and changes in the shape of the ventricle. The finite element model calculates this change in shape of the ventricle and also calculates how this change has affected the other structural elements of the ventricle and the heart. As the model reshapes the ventricle to make it smaller, it may show the effect reshaping has on the other structures like the mitral apparatus. The model may show the new location of the papillary muscles, new angle of the chordae tendinae to the mitral annulus, etc. The finite element model may use known methods described previously to calculate the reaction of different structural elements to changes in another element. For example, the geometric alterations may in turn have effects on various other cardiac performance characteristics i.e. smaller ventricles may have lower wall stress and may result in better contractility. The model may prompt the user to choose a patch to cover the opening that may be left in the ventricle and to reinforce the septum, FIG. 13L. If the opening in the ventricle is small, less than 3 centimeters, the model may tell the user to close the opening in the ventricle without a patch. The user may identify the suture placement locations as described previously and specify the amount of tension to be placed on the sutures. The model may depict the opening being closed with these sutures. The model may accomplish closing of the opening by taking the boundary layers at the edge of the opening and moving them towards each other. When the boundary layers meet, the model recalculates the finite element model shapes that should depict this closure area. For example if the finite element model is made of triangles the triangles on the boundary layer may be smaller than the average triangle in the model. When the two smaller triangles on the boundary layers meet at the closure line the smaller triangles may be combined into one average sized triangle. The finite element model may then interact with the outcomes predictor (30). The outcomes predictor may be composed of but not limited to a hemodynamic model (30a), a physiological model (30b), and/or other calculations (30c). These models may interact until the physiological and hemodynamic models are within tolerances of know physiological and hemodynamic constraints and/or balanced (32). The acceptance criteria may be SVI (stroke volume index) to be between 22 to 50 ml/mt$^2$ and that PAP (pulmonary artery pressure) to be within 10 to 25 mmhg, and ejection fraction to be above 30% and ESVI (end systolic volume index) to be between 25 and 60 ml/mt$^2$. If after 50 attempts, for example, the models cannot become balanced; the model may ask the doctor to alter his intervention. Once the models are balanced, the model may display the ventricle with the new shape and volume to the doctor along with potential clinical outcomes such as ejection fraction, mitral regurgitation etc. (34)(35). The doctor may accept these clinical outcomes (36) or return to the original model and image (37) and try a new treatment or modify the initial treatment. The doctor may perform multiple iterations of the procedure and compare clinical outcomes to determine which procedure is optimal for the patient (36). When the doctor accepts the intervention that is optimal for the patient, the model may then create specifications to help the doctor translate the simulated intervention to an actual procedure (38). The model may determine the size, shape, and/or volume of the ventricle desired. A unique shaping and sizing device may be created for the patient from the information to assist the doctor in performing the procedure (39).

Figure 17:
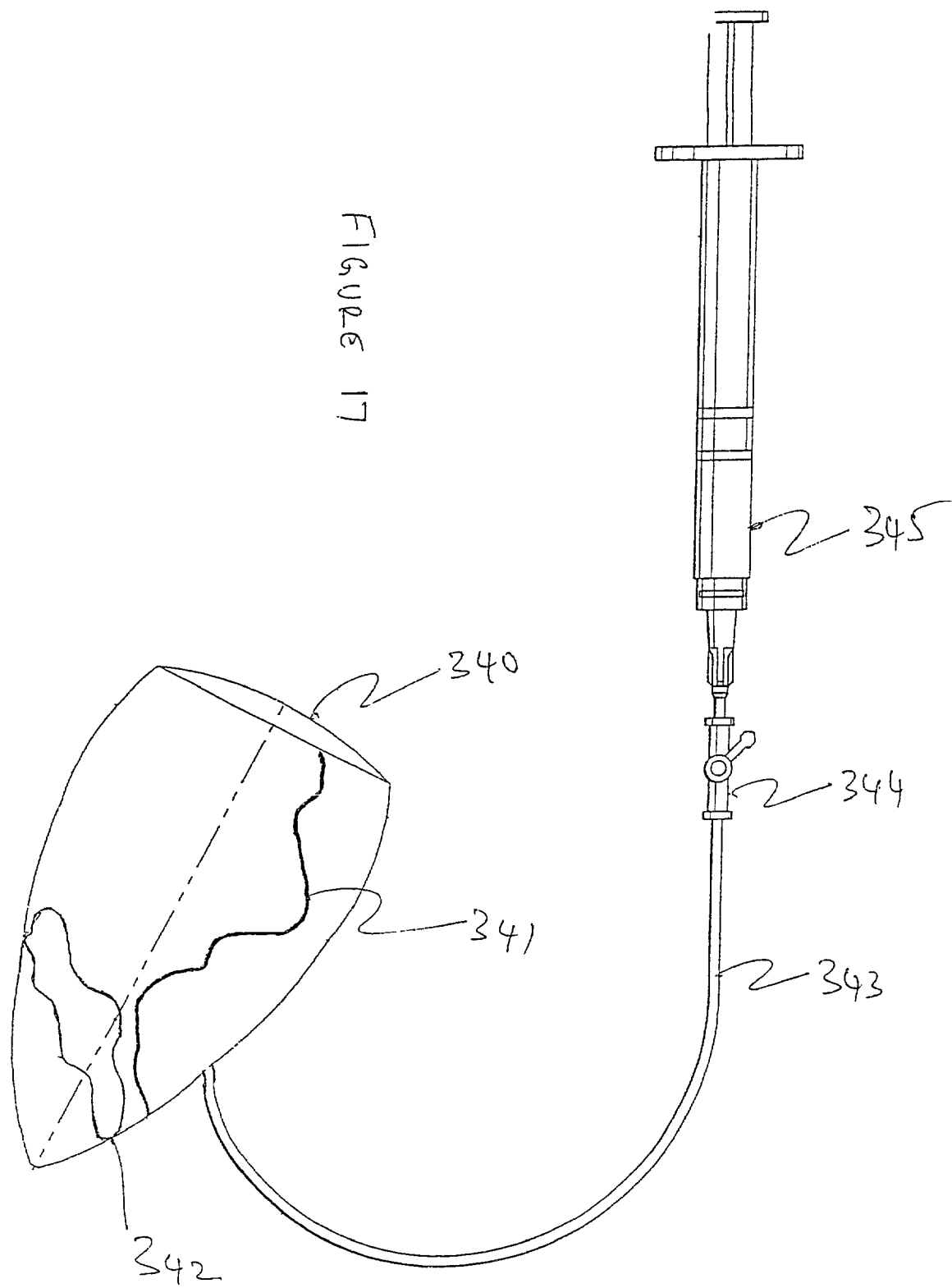
FIG. 17: Illustrates an embodiment of a sizing and shaping device with a location of a diseased area of a ventricle marked on its surface.
Figure 18:
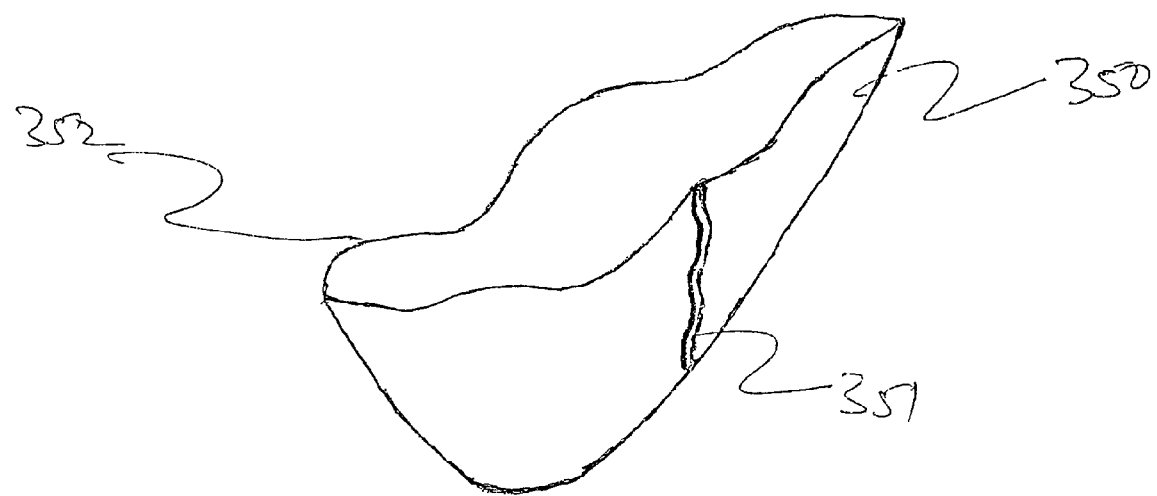
FIG. 18: Illustrates an embodiment of a pre-cut shape to allow a doctor to identify on a heart a diseased tissue.
Figure 20:
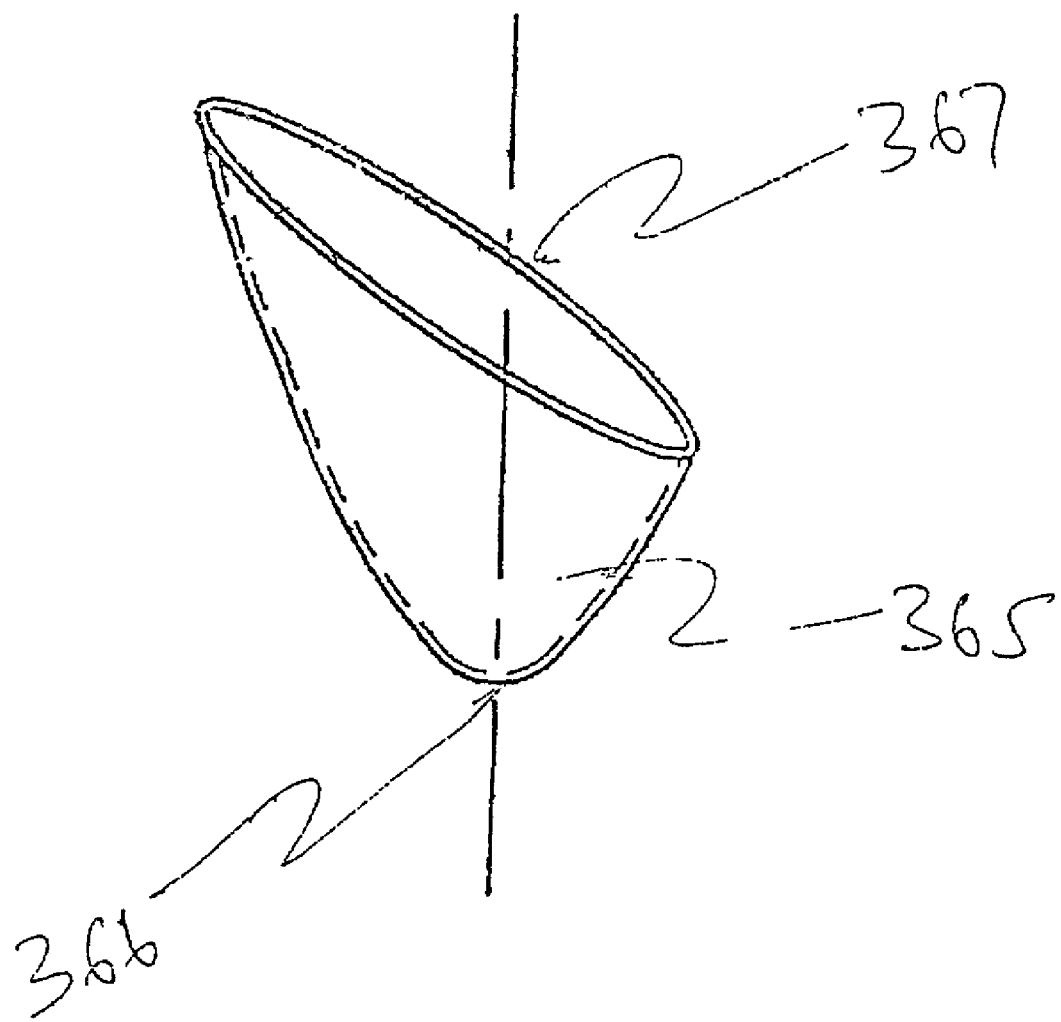
FIG. 20: Illustrates an embodiment of a patch that has apical shape.

In an embodiment, a method to make a custom sizing and shaping device is by generating a 3D CAD file (DXF or STL formats) that has the outline of the interior of the ventricle and load this file into a CNC milling machine. This machine may take the file and create a 3-Dimensional mandrel from the file. This mandrel may then be dipped in a number of solutions such as plastisol and urethane to form a pliable balloon like object that may be taken off the mandrel. A cap of similar material may be added to the top and a tube for filling the shaping and sizing device with fluid may be added, FIG. 17. The best solution to reconstruct the ventricle may require the use of a patch to reinforce the septum and/or close a hole remaining in the ventricle. The model may be able to show the doctor what shape patch may be needed to perform this task and a specially constructed patch may be made for this patient. A method to manufacture this custom patch could be to purchase cardiovascular patches currently sold by Boston Scientific/Meadox, or W. L. Gore, for examples. The model may generate a CAD file defining the shape of the opening in the ventricle. The shape of the opening may be printed and used as a template. The template could be placed on the patch and the patch cut to the shape and then sterilized FIG. 19. The model may lead to other tools that help the doctor implement the solution that the model has created like a patch with an apex etc FIG. 20.

In some embodiments, one way of performing an SVR procedure is to start of with a desired volume of the ventricle and selecting a ventricle sizer. The model may interact with the computational model of the ventricle sizer. These operations are similar to those mentioned in the earlier paragraph, except that the ventricle is formed over the ventricle sizer. The output of the model in this case may be a patient specific unique shaped patch that is needed to perform the intervention.

Figure 13H:
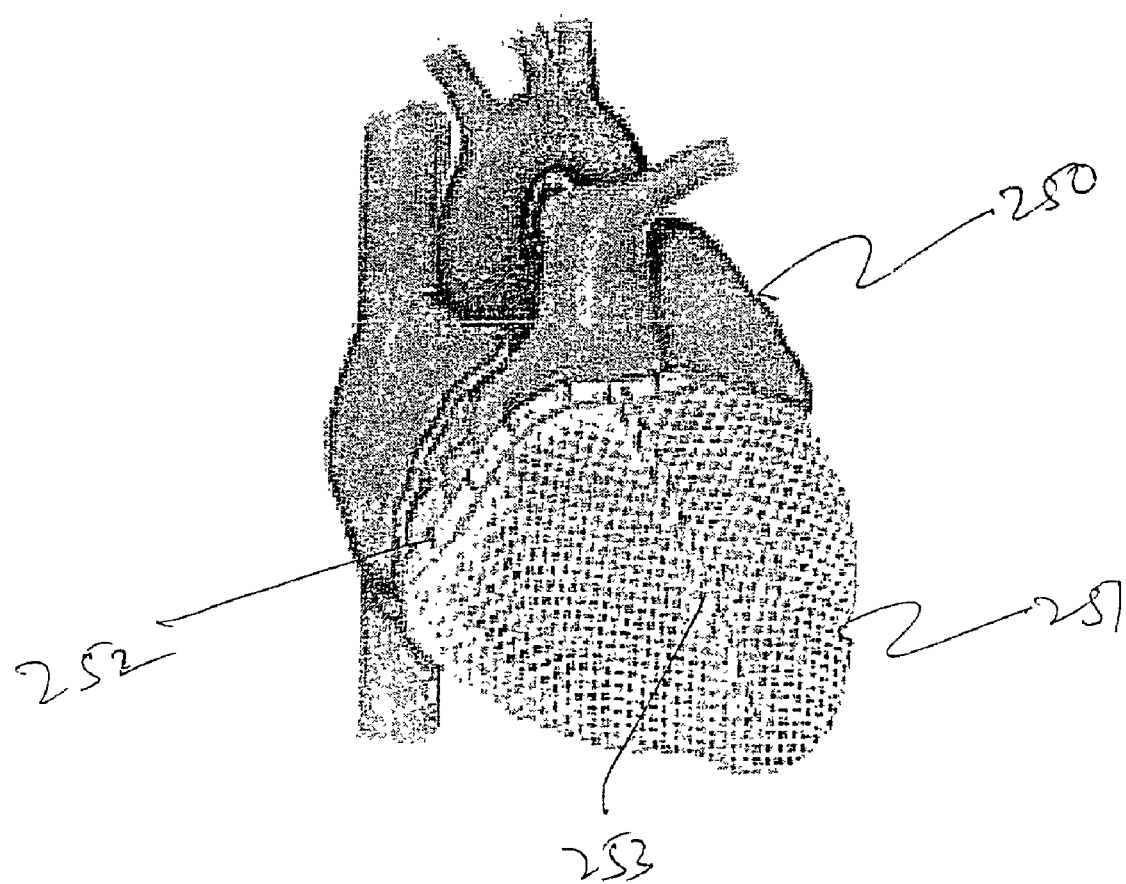
Figure 13:
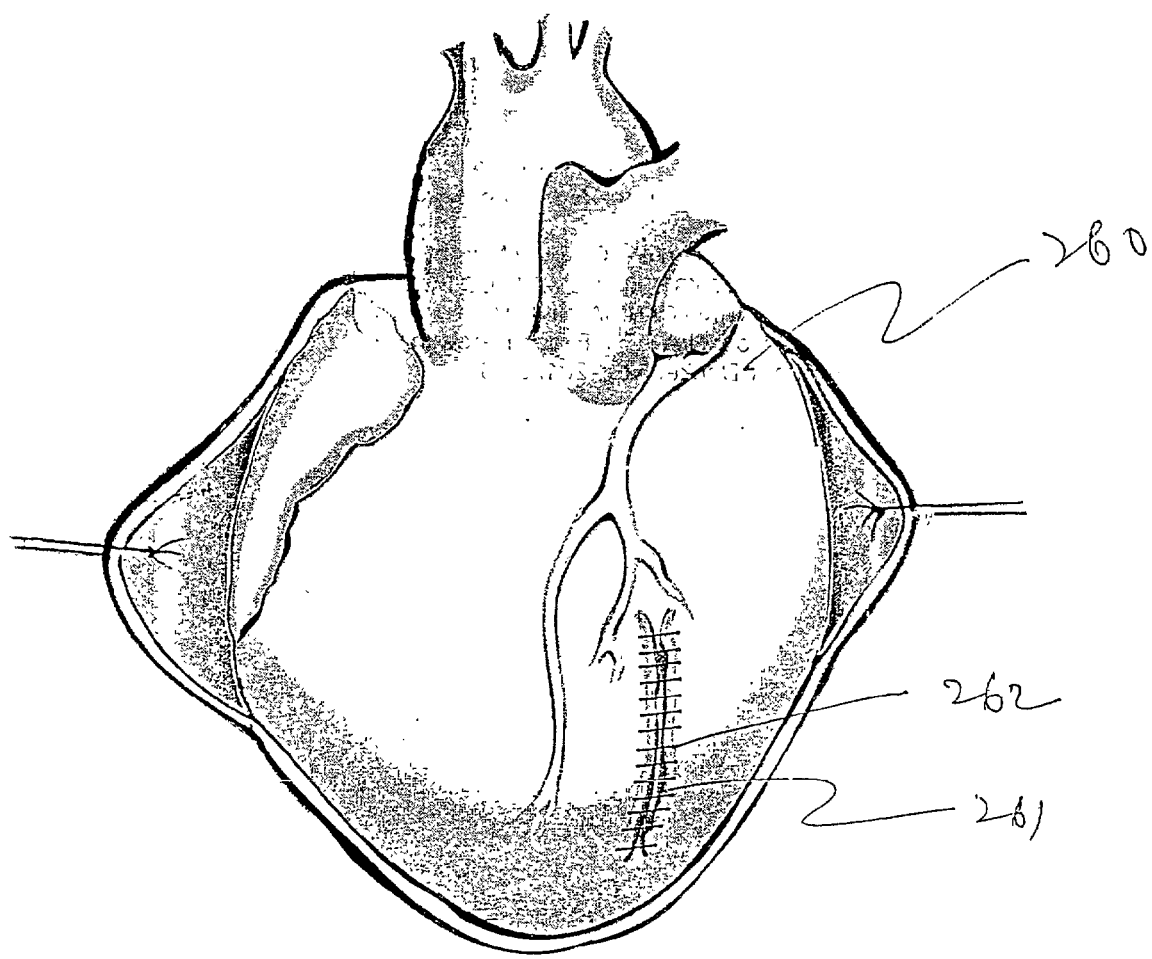
Figure 13J:
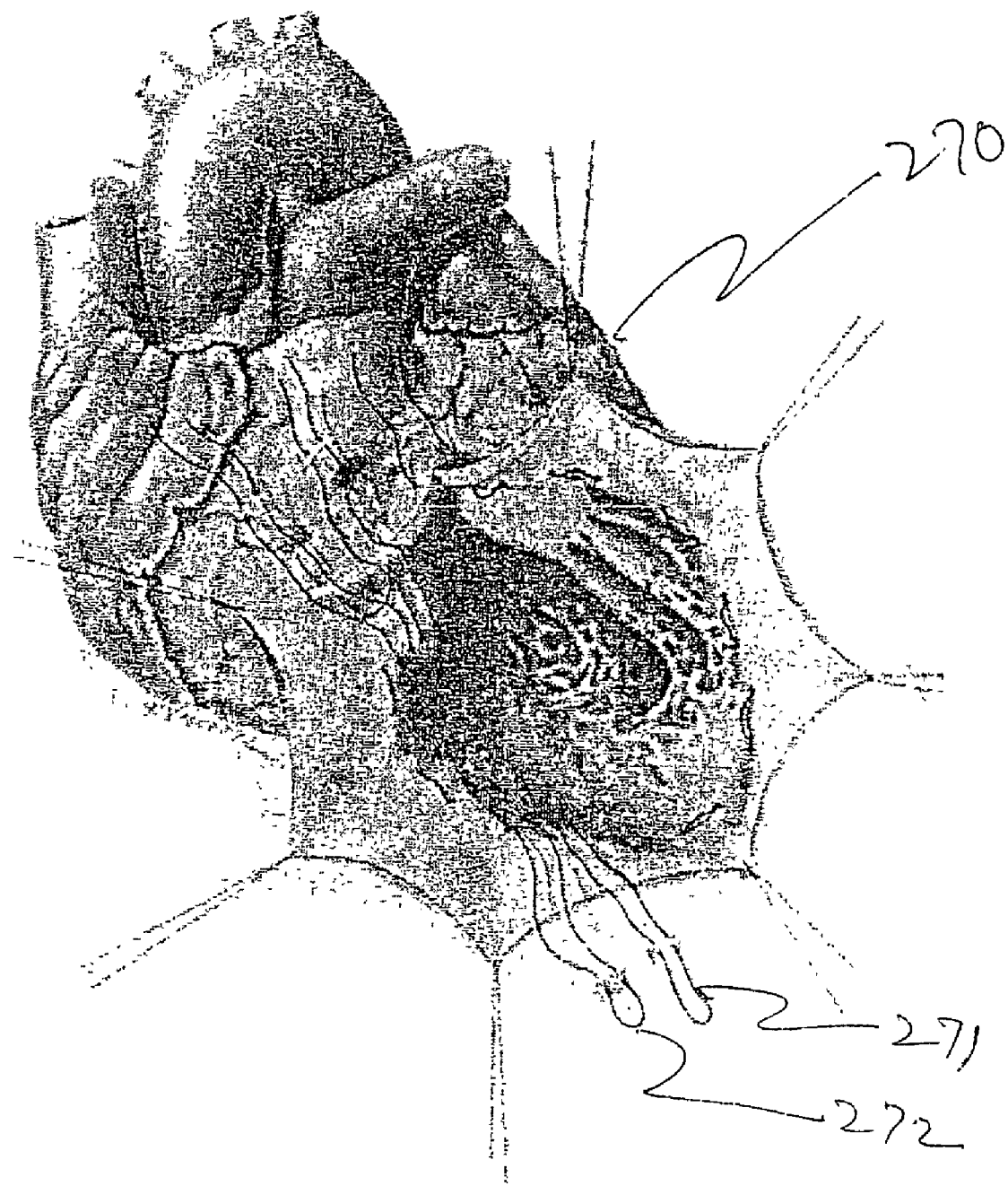
Figure 13K:
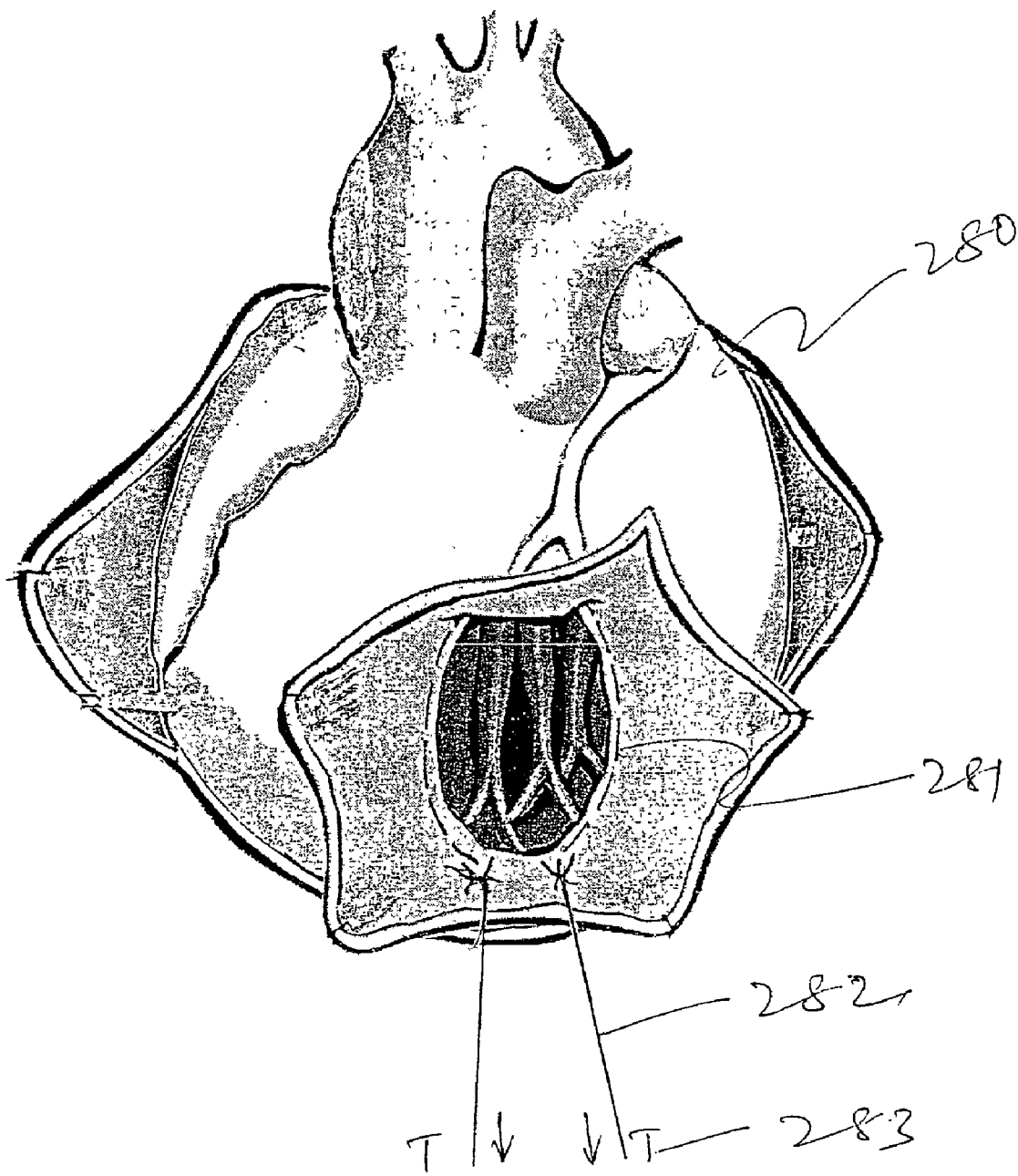
Figure 13L:
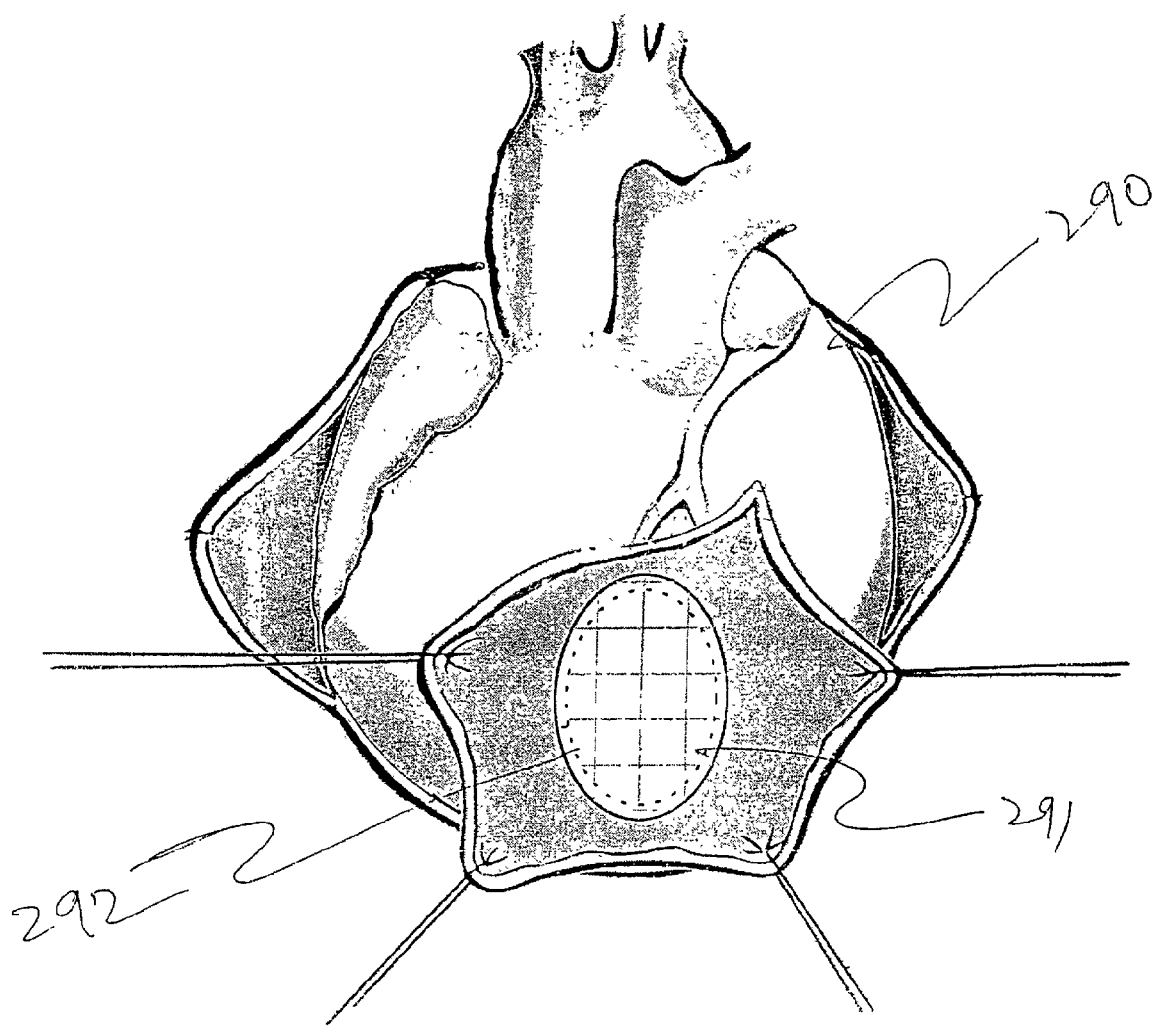
Figure 13:
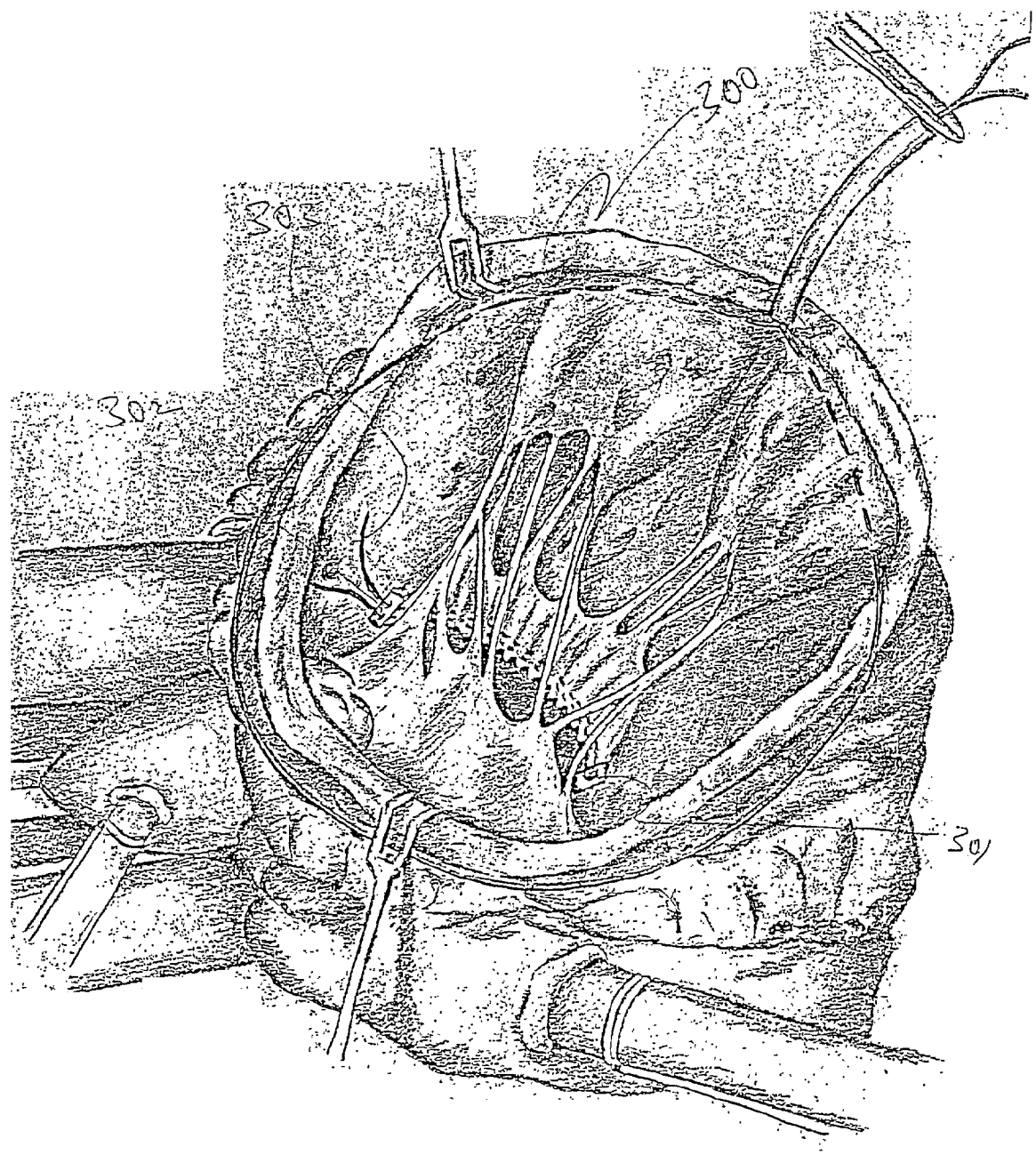
Figure 13N:
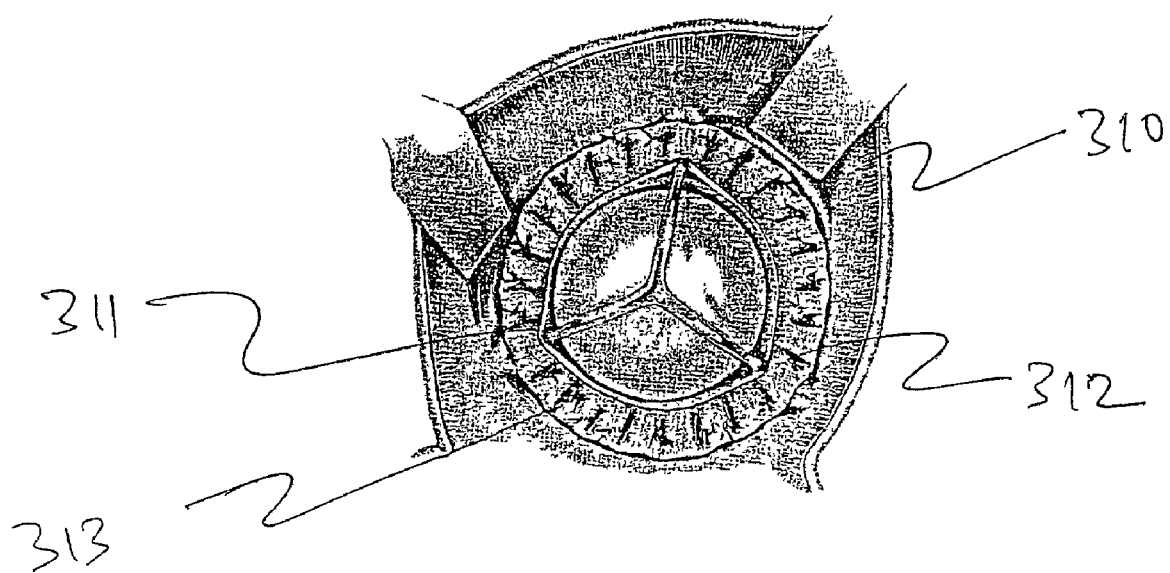

In some embodiments, a model may interact with finite element models of many currently marketed devices such as but not limited to the Myocor Inc Myosplint FIG. 13E, the Acorn Inc Corcap FIG. 13H or biventricular pacing from either Medtronic or Guidant may be made into a model. In each case the model may produce outcomes of the intervention with these devices. If the doctor likes the outcomes then specifications may be produced in order to transfer the results of virtual surgery to real surgery. In some instances specific tools or devices may be generated. The doctor takes these tools, devices and or specifications and conducts the procedure (39)

Figure 4:
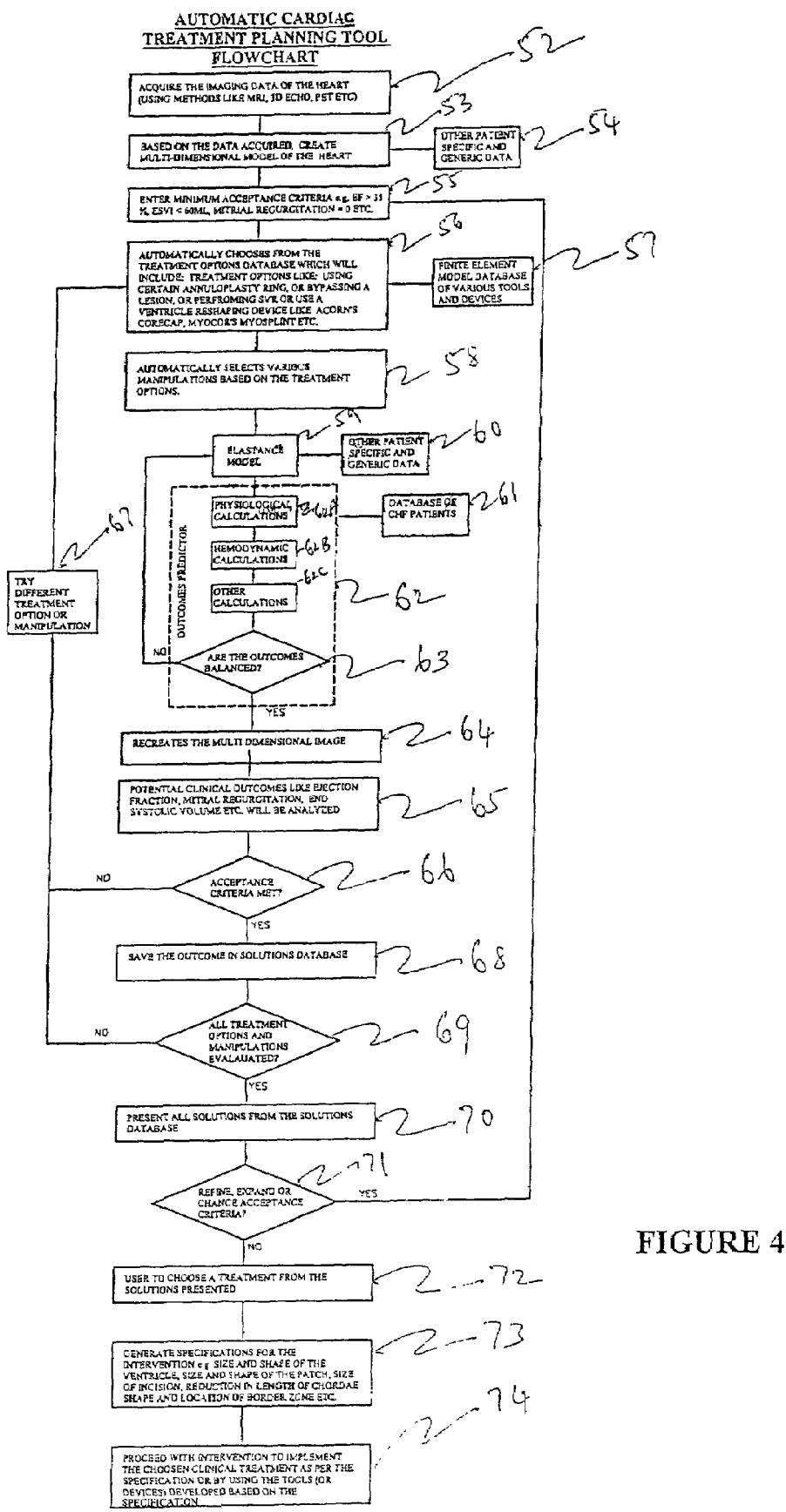
FIG. 4 is a flowchart illustrating one embodiment of a method of a cardiac intervention.

In an embodiment, a method and apparatus may also be used in an automatic mode, FIG. 4. A doctor could simply input a desired outcome or outcomes such as a defined ejection fraction range, ventricle volume range etc. Software may then run numerous iterations of all the different types of treatments and produce expected treatment options that meet defined criteria for that particular patient. Results may be ranked to allow the doctor to select the best treatment with the best outcome. The software may also just run and supply the best possible outcome without any input from a doctor besides the required data to run the software. The software may again present the doctor with expected outcomes prioritized. The software may report to the doctor that the desired outcome from a specific treatment is not possible and thereby force the doctor to reconsider his selection criteria options.

In some embodiments, before treatment, in order to determine which areas of the heart may need to be repaired or replaced, the patient may undergo an imaging procedure such as an MRI scan, PET scan or an Echocardiography scan to determine the location and condition of the components of the heart (10). The patient's current ventricular anatomical landmarks may be determined by manually tracing the epicardium and endocardium and/or it may be done by automated border detection software, which may quickly outline the location of different structures within the ventricle from the imaging data. This scan, with the borders delineated, is converted into a multi dimensional picture of the heart and may include all valves, arterial and venous structures of the heart (11). Parts of the valve apparatus, which may not fully appear with the automated border detection software (chordae tendinae) for example, may be quickly hand traced to complete the four dimensional dataset. The multi-dimensional image may also show regurgitation across the valves using different color gradients to show severity, as is currently done with echocardiography.

In some embodiments, post-treatment imaging such as MRI, PET and echocardiography scanning of the above listed measurement points may show the doctor how well the patient has done in treatment. The images of the patient's heart before treatment, the models depiction of the treated heart with performance characteristics may all be saved in a database. The doctor may compare the actual data with the predicted and determine how to improve his technique to achieve the theoretical best results. Long-term follow up is enhanced when current images of the heart may be compared to pre- and post-treatment images of the heart. These images may be analytically compared for small changes in the heart's geometry and alignment. If small changes are detected early, less invasive measures may be taken to stop or slow the progression of the abnormality. The surgeons may also use this database to pull up data on past patients who may have similar characteristics as the current patient under consideration, and compare his current treatment options to the past ones. Such methods may further contribute to improvement of techniques.

Figure 7:
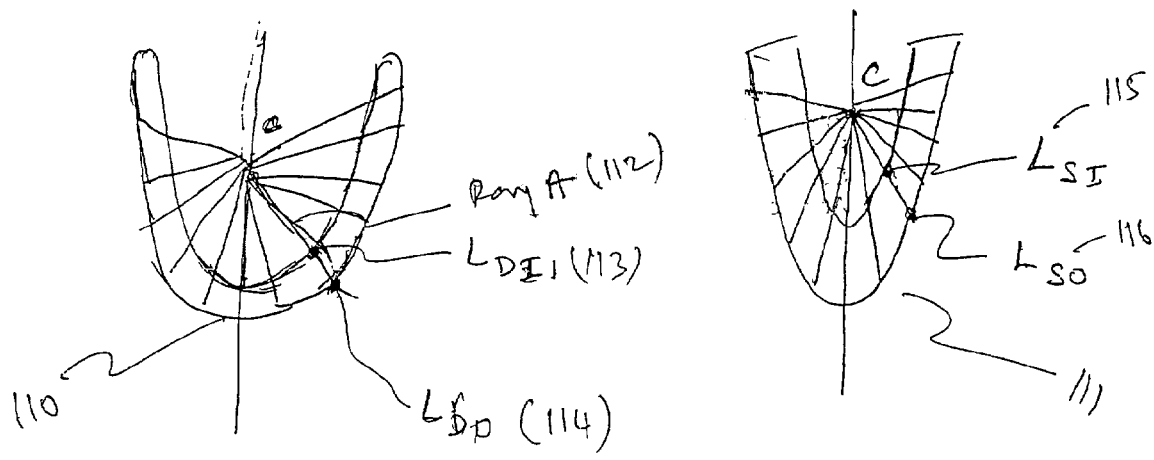
FIG. 7: Illustrates an embodiment of a comparison of systole and diastole images of a ventricle to show effect of wall thickening.
Figure 8:
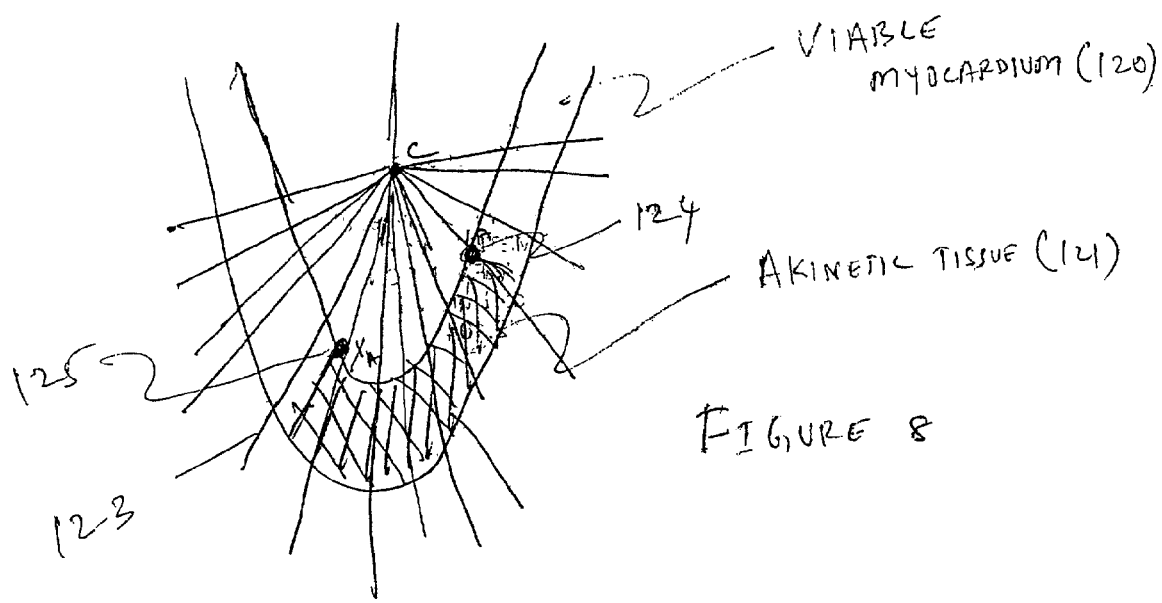
FIG. 8: Illustrates an embodiment of a comparison of systole and diastole images to determine border zone between a kinetic and functional tissue.

In an embodiment, one of the problems surgeons confront while doing SVR procedure is to determine, the demarcation line between viable and akinetic tissue. For this purpose a non-interactive model, which may show the location of diseased area of the ventricle may be used. The model may show on the image which areas of the ventricle are akinetic or dyskinetic to determine which areas might be excluded during SVR procedure. One method of doing this is to take the images from MRI or echocardiography FIG. 5. These images may be a combination of sections of the heart imaged during one cardiac cycle, so that each section contains a complete cycle, FIG. 5. These slices may be combined to create one image. The images at the end of systole and the end of diastole may be identified, FIG. 7. The images may be overlaid by aligning markers that don't move such as the aortic valve annulus and a grid pattern is then superimposed on these images, FIG. 8. Each intersection of the grid that intersects the epicardium and endocardium may be identified. The geometric center of the heart is calculated and imaginary lines (rays) are drawn from this center. Two points on each ray are recorded. Points are defined as points of intersection of the ray to the endocardium and epicardial boundary. For instance, $X_A$ and $Y_A$ are points on the border zone in this plane. The distance between these two points gives the wall thickness (d). Wall thickness is calculated on the diastole image $d_d$ and on the systole image $d_s$. As depicted in FIG. 7, the wall thickness at the diastole is $d_d = DL_{DO} - CL_{DI}$. Similarly, the wall thickness at the systole is $d_s = DL_{SO} - CL_{SI}$. Normally $d_s > d_d$ when the heart functions normally, because the myocardial wall thickens during systole to create pumping action. If a section of the heart muscle is diseased then $d_s = d_d$, meaning that portion of the wall is not thickening, it is referred to as akinetic tissue, it could be either dead or non-contributing tissue. All the rays that correspond to akinetic tissue are identified (all rays where $d_s = d_d$). The boundary layer of the akinetic area is then established by comparing each of the akinetic rays to its neighboring rays. For any given akinetic ray, if at least one of its neighboring rays is kinetic ($d_s > d_d$) then that akinetic ray is the boundary layer ray. Once all rays on the boundary layer are identified, the point of intersection of the boundary layer rays on the endocardial boundary defines the border zone between the viable and akinetic tissue.

In some embodiments, once the location of the diseased section is identified with respect to other cardiac structures, a 3D CAD file (DXF or STL files) may be generated which shows the location of the border area with respect to a known landmark on the heart. One may create a template that may match the diseased area and have anatomical landmarks from the heart such as Left Anterior Descending artery or the Atrial ventricular groove to ease alignment of the template to the diseased area. The template may be in a form of a balloon that is patient specific with the same shape and size as the interior of the ventricle, and with border zone marked on it or it may be a like a glove that fits on the outside of the heart with border zone and landmark points marked on it. Such tools may be very helpful in order execute SVR procedure with greater precision.

In an embodiment, a method to determine the diseased area of the ventricle is to measure the motion of the endocardium towards a centerline of the ventricle. This is popularly referred to as "centerline method" it determines the region of no motion by evaluation how much motion at 90 points of the ventricle the motion differs from the standard motion. In the centerline method any tissue that moves less than 2 standard deviations from a typical movement level of normal heart is considered diseased. This algorithm could be applied in the above-mentioned model to identify the border zone. The model may generate an image using different color gradients to depict the range of lack of motion from the standard. This color grading may give the doctor a precise location for tissue to exclude and may give assurance that the doctor will not exclude any viable tissue. A template showing the status of the myocardium stated above may be provided to the doctor to use as an aid in excluding the tissue. The gradient image may be used for both idiopathic and ischemic cardiomyopathy patient assessment.

Figure 21:
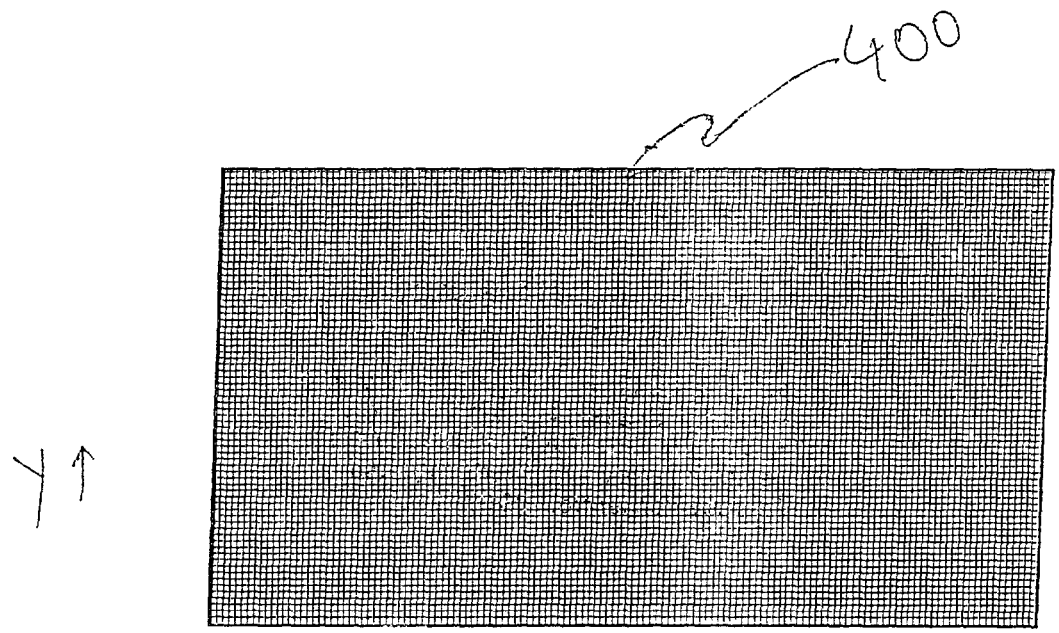
FIG. 21: Illustrates an embodiment of a patch with fibers that have strength in one axis different from a strength in another axis.

In some embodiments, when tissue is excluded as described herein, there may be a hole left in the ventricle that a surgeon will fill. One device that might cover this hole is a patch that could aid in the contraction of the left ventricle. One form of this patch may be made of a fabric that is pretensioned and stretched to fill the hole left in the ventricle. The pretensioning places stress on the fibers, which assist the ventricle in contraction when going back to their relaxed state during systole. Another variation could be that the short axis fibers are of a different strength than the long axis fibers, thus aiding the greater contraction along the short axis FIG. 21. The patch could have the pretensioned fibers only in the center of the patch, decreasing the tension exerted by the patch on the ventricle walls, but still providing some assistance to the ventricle during contraction.

Figure 3:
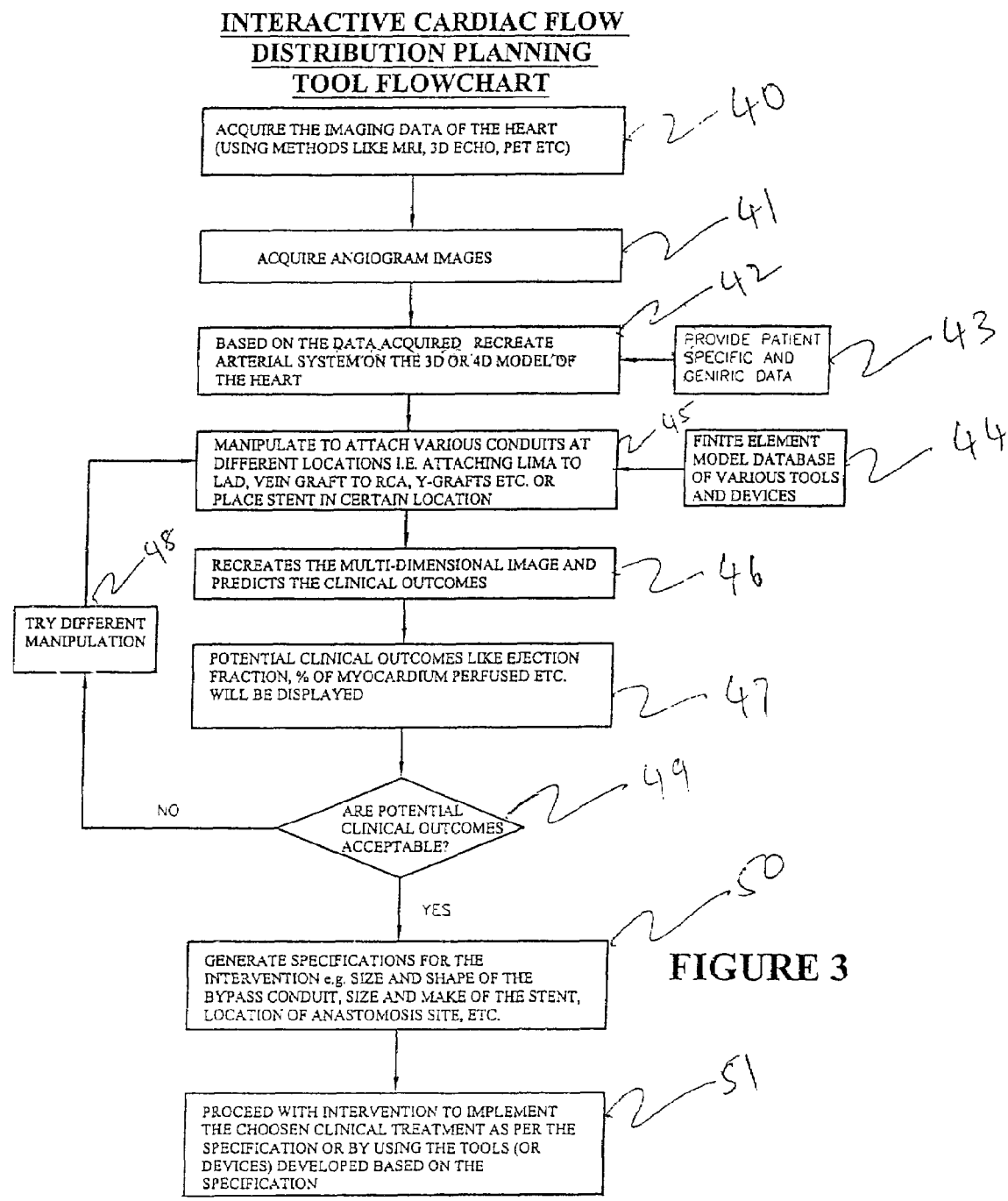
FIG. 3 is a flowchart illustrating one embodiment of a method of a cardiac intervention.

In an embodiment, an apparatus and method may be used to plan for bypass or stent interventions, FIG. 3 by showing the location and condition of the arterial system of the heart. Imaging of the arterial system with identification of lesions and blockage has been performed with ventriculograms. This process injects a dye into the aortic root, which supplies the cardiac arterial system with blood. The dye flows through the arterial system with the blood and may be imaged with X-rays to identify where the constricted points of the arterial vessels are located. The arterial system may then be mapped and a finite element model applied to the system to determine the width of the vessels, location of constrictions etc. to allow the model to predict how much blood is flowing to each portion of the heart. This may be correlated to displays of viable tissue, so that if the patient has had a myocardial infarction and has dead tissue, the doctor will not use the best graftable conduits FIG. 13F to graft to vessels feeding these areas or place stents on these vessels. Or perhaps the doctor will choose to not graft or stent at all. This model may give the doctor the opportunity to place different grafts or stents on different vessels to analyze the perfusion effect on the heart for the different combinations. The grafts or stent models may come from the database of surgical equipment and devices discussed previously (22). The model may then be run to show the doctor the effect that his grafts or stents may likely have on the entire cardiac and circulatory system, so that he may select the best combination of locations for that particular patient.

In an embodiment, an apparatus and method may be used to show the effects that interventions on the left vent outflow tract and aortic valve may have on other elements and/or the entire heart. The outflow tract changes position as people age and an acute angle in the left vent outflow tract may contribute to poor performance of the ventricle and/or the aortic valve. The model may show the positioning of the left vent outflow tract and may show the doctor turbulence or restrictions in blood flow through this area. There are many companies that have developed flow dynamic software. One such model was developed CDFRC (Huntsville, Ala.) and published by Makhijani et. al. "Three-dimensional coupled fluid—Structure simulation of pericardial bioprosthetic aortic valve function", ASAIO Journal 1997; 43:M387-M392. If desired the doctor may virtually manipulate the left vent outflow tract into different positions and then run the models to see which position of the tract provides the best flow dynamics. This may then tell the doctor if he needs to adjust the positioning of the left vent outflow tract and may show the effects that this new position will have on the performance of the heart. Poor performance of the aortic valve may limit the amount of blood that the ventricle may eject. The model may display the aortic valve and allow the doctor to virtually manipulate the valve and assess if the manipulations have increased the performance of the valve and increased the performance of the cardiac system. The doctor may then take the best results and perform those manipulations on the actual valve.

In an embodiment, a method and apparatus may be used to simulate the effects of drugs on the heart and its components. A database of drugs and their effects may be developed and the doctor may interact with the model by selecting a type of drug and dosage amount. The model may then give the doctor the results of the treatment, whether it has resulted in a change in the geometry of the heart and its components and if the performance of the heart has improved. For example the model may simulate the effects of vasodilators that may diminish the afterload of the heart or the effect of norepinephrine, which increases the contractility of the heart.

In some embodiments, a method and apparatus may be used to simulate the placement of mechanical devices in and/or on the heart to determine the benefits of the devices. The physical and functional characteristics of these devices may be determined through testing and may be reduced to a finite element model. These finite element models may be placed in a database. The doctor will interact with the model by choosing the device by its common name or product name, for example Myosplint or Corecap FIGS. 13E, 13H. He may direct its placement by methods described above specifying for example, location, attachment means etc. Left ventricular assist devices may also be added to the database. All these mechanical devices may be simulated to show their effects on the whole heart and its components. Effects may be compared to other less invasive treatments to determine if the increased invasiveness and cost of these devices is warranted by a corresponding increase in the heart's performance.

In some embodiments, a model may be accessed at a central location and the images of pre- and post-treatment images may be stored and categorized by disease type, surgical procedure, outcome, etc. may also be stored at this location. This database may be used to perform retrospective studies on the efficacy of different procedures and approaches for different disease states and patients. This database and analysis may contribute to the advancement and refinement of models and help improve their reliability. The database may be used to analyze treatments to compare and empirically demonstrate which are the best treatments for certain patients. The database may allow doctors to compare their results with the database population. The doctor may be able to see if his selection of and performance of treatment options is better, equal to, or worse than the group as a whole. If he is worse than the group, the surgeon may use the database to help improve his treatment selection making process and his technique.

In an embodiment, an improved apparatus and method is provided for capturing the geometry of the heart and its components using imaging technologies such as, but not limited to, MRI imaging, echocardiography, or PET (10). Using imaging information along with other factors may be used to create a multi-dimensional finite element computer model of the heart (11). The model may display not only the three dimensions of the geometry of the heart but may also depict this geometry as it changes over time. This model may run on a personal computer type of machine, it may run at a central location, and/or it may be processed at one location and delivered to another location to be run. The multi dimensional model may allow the doctor to visually inspect the status of all the elements of the heart. This model may be used to determine a variety of information, either pre-treatment, during the treatment, and/or post-treatment, including, but not limited to:

a. The areas of the mitral apparatus, aortic, tricuspid or pulmonary valves that may need to be repaired or replaced and what affect each repair may have on the other components.

b. What vessels are blocked and may need to be grafted, where to graft and what affect the revascularized muscle may have on the other components.

c. What areas of the ventricle are akinetic, dyskinetic or hibernating, to show what areas may be excluded during ventricular restoration and what effect the exclusion may have on the other components and aspects of the ventricle and heart.

d. How the patient's heart may respond to medication treatment.

e. The effects of placement of an Acorn, Myocor or other device on the outside of the ventricle may affect the heart.

f. The effects of chordae length adjustment or papillary base relocation may affect the heart.

g. The effects of placement of any ventricular assist device may have on the heart.

h. What vessels are blocked and may need to be stented, where to stent and what affect the revascularized muscle may have on the other components.

In an embodiment, a model may allow the doctor to select a treatment option (12) and allow the doctor to manipulate the image and model (13). The model may analyze what effects his virtual treatment may likely have on the cardiac system. The model may display the potential clinical outcomes to the doctor (14), (16). The potential outcomes display may be but are not limited to the following (17):

a. The estimated performance of the valves and ventricle after the procedure; i.e. regurgitation, reduced flow across the valves, ejection fraction etc.

b. The volume and contractile state of the ventricle after excluding tissue.

f. The positioning and performance of the valve apparatuses after reconstruction of the ventricle.

In an embodiment, a doctor may be able to select the displayed intervention (18), decide to try another treatment, and/or modify the current intervention (19) and the cycle may repeat itself. When the doctor accepts the potential clinical outcomes, the model may then produce the specifications for the intervention (20). Specifications may lead to the development of templates, tools, and/or devices to guide the doctor in translating the virtual intervention on the model to the actual intervention on the heart. No template or devices may be needed to perform the intervention and specifications such as the length of a chordae tendinae may be sufficient output from the model to allow the doctor to perform the intervention. Additional devices may be generated from the models to help the doctor implement the procedure that the model may have predicted to provide the best outcome. Devices may include prosthetic mitral apparatus that is patient specific, or a customized annuloplasty ring etc (21). Use of some or all of above listed factors may be used to evaluate, post-treatment, the condition of the patient. A database of surgical pathologies, treatments and outcomes may be gathered, maintained and analyzed to further refine the treatment of cardiac diseases and disorders.

In an embodiment, a model may assist in determining before the treatment what likely effects his treatment of one or more elements of the heart will have on the other elements, and how to optimize the treatment of each component relative to the other components in order to achieve the best performance of the entire cardiac and circulatory system. The method and apparatus should allow the doctor to simulate numerous interventions and allow him to compare the different simulations, so that he may perform the option that gave him the best outcome. Interventions may include but are not limited to; placement of a Myosplint (Myocor Inc., Maple Groove, Minn.), placement of Corcap restraining device (Acorn cardiovascular Inc, St. Paul, Minn.), valve replacement (St. Jude Medical, St. Paul, Minn.), annuloplasty (Edward Lifesciences, Irvine, Calif.), surgical ventricular restoration (Chase Medical, Richardson, Tex.) stent placement (Medtronic, Minneapolis, Minn.), valve repair (Edward Lifesciences, Irvine, Calif.), bypass grafting, pacing, Biventricular pacing (Medtronic, Minneapolis, Minn.) and ventricle assist device (Abiomed, Danvers, Mass.). Surgical Ventricular Restoration (SVR) may be improved by providing a method and apparatus where a doctor may take an image of the patient's heart or ventricle and create an interactive multidimensional model with structural elements. The doctor may manipulate the model by deleting, adding or rearranging the structural elements to simulate the SVR procedure. The model may integrate all the manipulations relative to each other and then interact with other models such as but not limited to physiological and hemodynamic models. The interactive multidimensional model may recreate the patient's heart or ventricle based on the manipulations conducted by the doctor and depict the new ventricle or heart and display cardiac performance characteristics and parameters. The doctor may perform this simulation numerous times and then compare the performance characteristics and select the optimal procedure. The model may produce specifications for the selected procedure from which templates or tools may be created to aid the doctor in translating the virtual procedure to the real procedure.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

The invention claimed is:

1. A method of diagnosing a human heart, comprising:
providing to a computer system a plurality of first images of heart tissue from the heart;
using the plurality of first images to create at least one second image of human heart tissue using the computer system, comprising:
creating endocardial and epicardial left ventricle wall contours;
automatically segmenting at least a portion of left ventricle wall endocardial contours of at least two of the provided images of heart tissue into a selected number of endocardial left ventricle wall points;
automatically segmenting at least a portion of left ventricle wall epicardial contours of at least two of the provided images of heart tissue into a selected number of epicardial left ventricle wall points; and
automatically using endocardial left ventricle wall points and epicardial left ventricle wall points to create a model of at least a portion of the left ventricle wall over one or more periods of time;
wherein the second image comprises one or more structural elements; and
comparing at least one structural element to one or more heart reference structural elements in a database to assess a state of the heart.

2. The method of claim 1, wherein at least one of the reference structural elements comprises an image.

3. The method of claim 1, wherein at least one of the reference structural elements comprises a portion of an image.

4. The method of claim 1, wherein at least one of the reference structural elements comprises a physiological factor.

5. The method of claim 1, wherein at least one of the reference structural elements comprises a numerical element.

6. The method of claim 1, wherein at least one of the reference structural elements comprises a numerical element derived at least in part from at least a portion of an image.

7. The method of claim 1, wherein comparing at least one structural element comprises using the computer system to perform the comparison.

8. The method of claim 1, wherein the database comprises data from one or more surgical procedures.

9. The method of claim 1, wherein the computer system divides the plurality of first images into a plurality of sections.

10. The method of claim 1, further comprising extrapolating at least a portion of at least one structural element from the plurality of first images of human heart tissue provided to the computer system.

11. The method of claim 1, further comprising using the plurality of first images to create at least a second image, wherein at least a portion of the second image appears at least four-dimensional.

12. The method of claim 11, wherein one of the four-dimensions comprises time.

13. The method of claim 11, wherein at least one of the four-dimensions comprises at least one physiological factor.

14. The method of claim 13, wherein at least one physiological factor comprises hormone B-type natriuretic peptide.

15. The method of claim 1, further comprising creating one or more images of the assessed state of the heart.

16. The method of claim 15, wherein at least one image of the assessed state of the heart comprises at least a portion appearing at least three-dimensional.

17. The method of claim 15, wherein at least one image of the assessed state of the heart comprises color gradients.

18. The method of claim 1, further comprising creating endocardial and epicardial left ventricle wall contours automatically.

19. The method of claim 1, further comprising using the model of the portion of the left ventricle wall over time to assess left ventricular wall thickness over time.

20. The method of claim 1, further comprising automatically comparing the model of at least a portion of the left ventricle wall with one or more corresponding portions of reference left ventricle wall in a database.

21. The method of claim 1, further comprising automatically comparing the model of at least a portion of the left ventricle wall with one or more corresponding portions of reference left ventricle wall in a database, wherein the reference left ventricle wall comprises an equivalent number of corresponding portions such that the model may be directly compared to the reference left ventricle wall.

22. The method of claim 1, further comprising automatically comparing the model of at least a portion of the left ventricle wall with one or more corresponding portions of reference left ventricle wall in a database, wherein the reference left ventricle wall comprises the selected number of epicardial left ventricle wall points and the selected number of endocardial left ventricle wall points.

23. The method of claim 1, further comprising using the model to automatically assess wall thickness over time of the left ventricle.

24. The method of claim 1, further comprising using the model to automatically assess areas of abnormal movement in the left ventricle.

25. The method of claim 1, further comprising assessing one or more portions of the left ventricle to recommend for exclusion during a surgical procedure.

26. The method of claim 1, further comprising:
automatically comparing the model of at least a portion of the left ventricle wall with one or more corresponding portions of reference left ventricle wall in a database; and
automatically assessing a state of the human heart.

27. The method of claim 1, further comprising:
automatically comparing the model of at least a portion of the left ventricle wall with one or more corresponding portions of reference left ventricle wall in a database;
automatically assessing a state of the human heart; and
automatically creating one or more images of the assessed state of the heart.

28. The method of claim 1, further comprising automatically comparing the model of at least a partition of the left ventricle wall with one or more corresponding portions of reference left ventricle wall in a database, wherein the reference left ventricle wall is derived from clinical data.

29. The method of claim 1, further comprising automatically comparing the model of at least a partition of the left ventricle wall with one or more corresponding portions of reference left ventricle wall in a database, wherein the reference left ventricle wall is derived from one or more surgical procedures.

30. The method of claim 1, wherein the model appears at least three-dimensional.

31. The method of claim 1, wherein the model appears at least four-dimensional.

32. A method of diagnosing a human heart, comprising:
providing two or more sectional views of heart tissue from the heart to a computer system;
creating endocardial and epicardial left ventricle wall contours;
automatically segmenting at least a portion of left ventricle wall endocardial contours of at least two of the sectional views into a selected number of endocardial left ventricle wall points;
automatically segmenting at least a portion of left ventricle wall epicardial contours of at least two of the sectional views into a selected number of epicardial left ventricle wall points;
automatically using endocardial left ventricle wall points and epicardial left ventricle wall points to create a model of at least a portion of the left ventricle wall over one or more periods of time; and
automatically comparing the model of at least a portion of the left ventricle wall with one or more corresponding portions of reference left ventricle wall in a database; and
automatically assessing a state of the human heart.

33. The method of claim 32, further comprising creating endocardial and epicardial left ventricle wall contours automatically.

34. The method of claim 32, further comprising using the model of the portion of the left ventricle wall over time to assess left ventricular wall thickness over time.

35. The method of claim 32, wherein the reference left ventricle wall comprises an equivalent number of corresponding portions such that the model may be directly compared to the reference left ventricle wall.

36. The method of claim 32, wherein the reference left ventricle wall comprises the selected number of epicardial left ventricle wall points and the selected number of endocardial left ventricle wall points.

37. The method of claim 32, further comprising using the model to automatically assess wall thickness over time of the left ventricle.

38. The method of claim 32, further comprising using the model to automatically assess areas of abnormal movement in the left ventricle.

39. The method of claim 32, further comprising assessing one or more portions of the left ventricle to recommend for exclusion during a surgical procedure.

40. The method of claim 32, further comprising automatically creating one or more images of the assessed state of the heart.

41. The method of claim 32, wherein the reference left ventricle wall is derived from clinical data.

42. The method of claim 32, wherein the reference left ventricle wall is derived from one or more surgical procedures.

43. The method of claim 32, wherein the model appears at least three-dimensional.

44. The method of claim 32, wherein the model appears at least four-dimensional.

* * * * *